United States Patent
Kim et al.

(10) Patent No.: US 9,492,076 B2
(45) Date of Patent: Nov. 15, 2016

(54) DUAL FOCUSING OPTICAL COHERENCE IMAGING SYSTEM

(75) Inventors: Beop Min Kim, Seoul (KR); Hyun Woo Jeong, Seoul (KR); Sang Won Lee, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 475 days.

(21) Appl. No.: 13/980,973

(22) PCT Filed: Jan. 30, 2012

(86) PCT No.: PCT/KR2012/000698
§ 371 (c)(1),
(2), (4) Date: Jul. 22, 2013

(87) PCT Pub. No.: WO2012/105780
PCT Pub. Date: Aug. 9, 2012

(65) Prior Publication Data
US 2013/0301006 A1    Nov. 14, 2013

(30) Foreign Application Priority Data

Feb. 1, 2011  (KR) .................. 10-2011-0010155
Jan. 18, 2012 (KR) .................. 10-2012-0005919

(51) Int. Cl.
*A61B 3/14* (2006.01)
*A61B 3/10* (2006.01)
(Continued)

(52) U.S. Cl.
CPC .......... *A61B 3/102* (2013.01); *A61B 5/0066* (2013.01); *G01B 9/02021* (2013.01); *G01B 9/02027* (2013.01); *G01B 9/02044* (2013.01); *G01B 9/02091* (2013.01)

(58) Field of Classification Search
CPC ...... A61B 3/14; A61B 3/0025; A61B 3/102; A61B 3/12; A61B 3/113; A61B 3/152; A61B 3/0058; A61B 3/0033; A61B 3/0041; A61B 3/0008; A61B 3/1005; A61B 3/103; A61B 3/0091; A61B 3/10; A61B 3/1225; A61B 3/13; A61B 3/032; A61B 3/008
See application file for complete search history.

(56) References Cited

U.S. PATENT DOCUMENTS

2006/0109423 A1* 5/2006 Wang ................. A61B 3/101
                                              351/206
2010/0091243 A1* 4/2010 Bor .................... A61B 3/102
                                              351/219

(Continued)

FOREIGN PATENT DOCUMENTS

JP    2008-128707 A    6/2008
JP    2010-167268 A    8/2010

(Continued)

OTHER PUBLICATIONS

Stic Search Report.*

*Primary Examiner* — Pascal M Bui Pho
*Assistant Examiner* — Sharrief Broome
(74) *Attorney, Agent, or Firm* — Rabin & Berdo, P.C.

(57) ABSTRACT

The present invention relates to a dual focusing optical coherence imaging system. The dual focusing optical coherence imaging system includes: a light source unit for generating broadband light; a main optical distributor for distributing the light generated from the light source to allow the light to be propagated; an interference unit including first and second interference parts for forming interference signals with respect to different focused areas of an object to be detected using the light distributed from the optical distributor, and a common sample arm commonly connected to the first and second interference parts; an optical switch connected to the first and second interference parts to select at least one of the interference signals transmitted from the first and second interference parts; and a detection unit for converting the interference signal selected by the optical switch according to a preset mode into an electrical signal.

20 Claims, 10 Drawing Sheets

(51) Int. Cl.
*G01B 9/02* (2006.01)
*A61B 5/00* (2006.01)

(56) References Cited

U.S. PATENT DOCUMENTS

2011/0228222 A1 9/2011 Kobayashi

2012/0026464 A1 2/2012 Berger et al.

FOREIGN PATENT DOCUMENTS

| JP | 2010-268990 A | | 12/2010 |
|---|---|---|---|
| JP | 2010268990 A | * | 12/2010 |

* cited by examiner

DUAL FOCUSING OPTICAL COHERENCE IMAGING SYSTEM

TECHNICAL FIELD

The present invention relates to an optical coherence imaging system, and particularly to, an optical coherence imaging system configured to have a compact structure, which enables acquisition of video information for a plurality of focused areas of a single object to be detected through a single scan operation.

BACKGROUND ART

In general, an optical coherence tomography (OCT) is one of advanced medical imaging technologies that currently come into the significant spotlight in the market. The optical coherence tomography (OCT) possesses a representative advantage in that it can perform a tomographic imaging of the inner microstructure of a biological tissue with a micro-high definition in a non-invasive and high-speed manner. Since an optical coherence tomography (OCT) for ophthalmic use for imaging of a retina was greatly successful in commercialization, the speed of the research has been accelerated on commercialization of various OCT-related products including an OCT for endoscopy, an OST for skin diagnosis, an OST for tumor diagnosis, and so forth around the world. In addition, researches are overly actively in progress on technologies for allowing the image acquiring speed to be made fast, acquiring high resolution images, reducing the manufacturing cost, minimizing the influence of noises, and so forth.

FIG. 1 is a basic schematic view illustrating a spectral domain optical coherence tomography (SD-OCT) system according to the prior art. A light source 21 employs a low-coherence broadband light source. For example, light source 21 employs a light source having a wavelength with a bandwidth of 800 nm and 1300 nm in the OCT for ophthalmic use. Light generated from the light source 21 is distributed to a reference arm where a mirror 22 is positioned and a sampled arm where an object to be examined is positioned while passing through an optical distributor 24. When the travel distance of light from the optical distributor 24 to the mirror of the reference arm is equal to the travel distance of light from the optical distributor 24 to the object to be examined of the sample arm, the light reflected from the mirror and the light reflected from the sample meet each other to generate an interference signal. The produced interference signal is incident on a spectrometer 26 and then is finally detected by a line scan camera via a diffraction grating and a lens.

A conventional OCT system for ophthalmic use is constructed as the above-mentioned basic system. The OCT system allows parallel light to be incident on an eyeball using two lenses in the sample arm and then to be focused on the retina by a crystalline lens present in the eyeball. There frequently occurs the case where the cornea and the retina are required for evaluation and diagnosis, but an OCT technology has not been proposed yet which can measure the cornea and the retina simultaneously.

That is, in case of the conventional OCT system for ophthalmic use, since the position of the mirror of the reference arm is fixed so that an image is acquired at a portion where a single focal point is formed by the lens of the sample arm, it is impossible to simultaneously measure the cornea and the retina that have different focused areas using a single spectrometer. The reason for this is that when the position of the mirror of the reference arm is set based on the focal formation distance of the retina, acquisition of video information with respect to the cornea is physically impossible due to a significant difference between the light travel distance from the optical distributor to the retina the light travel distance from the optical distributor to the cornea.

Further, the cornea is positioned in front of the crystalline lens in the eyeball, and the retina is positioned at the rear of the crystalline lens in the eyeball, so that when the parallel light is transmitted to the retina to acquire an image of the retina, a focus is not formed at the cornea, which makes it impossible to acquire an image of the cornea. Thus, an existing OCT system entails a problem in that it is designed for measurement of either the retina or the cornea, and two spectrometers are needed to solve this, leading to an increase in the number of the spectrometers, and thus a sharp increase in the manufacturing cost. This makes it difficult to achieve a compact structure of the OCT system.

DISCLOSURE OF INVENTION

Technical Problem

Accordingly, it is an object of the present invention to provide an optical coherence imaging system configured to have a compact structure, which enables acquisition of video information for a plurality of focused areas of a single object to be detected through a single scan operation.

Technical Solution

To achieve the above objects, in one aspect, the present invention provides a dual focusing optical coherence imaging system, including: a light source unit for generating broadband light; a main optical distributor for distributing the light generated from the light source to allow the light to be propagated; an interference unit including first and second interference parts for forming interference signals with respect to different focused areas of an object to be detected using the light distributed from the optical distributor, and a common sample arm commonly connected to the first and second interference parts; an optical switch connected to the first and second interference parts to select at least one of the interference signals transmitted from the first and second interference parts; and a detection unit for converting the interference signal selected by the optical switch according to a preset mode into an electrical signal.

In the dual focusing optical coherence imaging system, the first interference part may include: a first optical distributor for receiving the broadband light distributed from the main optical distributor; a first sample arm including a first sample arm collimator for receiving the light distributed from the first optical distributor; and a first reference arm including a first reference arm collimator for receiving the light distributed from the first optical distributor other than the light distributed to the first sample arm, and a first reference mirror for reflecting the light incident from the first reference arm collimator to allow the reflected light to return to the first optical distributor.

In the dual focusing optical coherence imaging system, the second interference part may include: a second optical distributor for receiving the broadband light distributed from the main optical distributor; a second sample arm including a second sample arm collimator for receiving the light distributed from the second optical distributor; and a second reference arm including a second reference arm collimator for receiving the light distributed from the second optical distributor other than the light distributed to the second sample arm, and a second reference mirror for reflecting the light incident from the second reference arm collimator to allow the reflected light to return to the second optical distributor.

In the dual focusing optical coherence imaging system, the first interference part may include: a first optical distributor for receiving the broadband light distributed from the main optical distributor; a first sample arm including a first sample arm collimator for receiving the light distributed from the first optical distributor; and a first reference arm including a first reference arm collimator for receiving the light distributed from the first optical distributor other than the light distributed to the first sample arm, and a first reference mirror for reflecting the light incident from the first reference arm collimator to allow the reflected light to return to the first optical distributor, the second interference part may include: a second optical distributor for receiving the broadband light distributed from the main optical distributor; a second sample arm including a second sample arm collimator for receiving the light distributed from the second optical distributor; and a second reference arm including a second reference arm collimator for receiving the light distributed from the second optical distributor other than the light distributed to the second sample arm, and a second reference mirror for reflecting the light incident from the second reference arm collimator to allow the reflected light to return to the second optical distributor, and the common sample arm may include: a common arm optical distributor for reflecting the light transmitted from the first optical distributor and the second optical distributor through the first sample arm collimator and the second sample arm collimator; a common arm optical scanner for irradiating the light reflected from the common arm optical distributor toward the different focused areas of the object to be detected; and a common arm objective lens for focusing the light irradiated from the common arm optical scanner to allow the focused light to be irradiated onto the different focused areas of the object to be detected, and re-transmitting the light reflected from the different focused areas of the object to be detected to the common arm optical scanner.

In the dual focusing optical coherence imaging system, the common sample arm may further include a first sample arm focusing lens between the first sample arm collimator and the common arm optical distributor.

In the dual focusing optical coherence imaging system, the first interference part may further include a first reference polarization controller provided between the first optical distributor and the first reference arm collimator, and the second interference part may further include a second reference polarization controller provided between the second optical distributor and the second reference arm collimator.

In the dual focusing optical coherence imaging system, the optical switch may be connected to the first optical distributor and the second optical distributor to receive the interference signals from the first optical distributor and the second optical distributor for transmission to the detection unit, and may include a switching polarization controller disposed at an at least one position of positions between the optical switch and the first optical distributor/the second optical distributor and a position between the optical switch and the detection unit.

In the dual focusing optical coherence imaging system, the common sample arm may further include a first sample arm focusing lens disposed between the first sample arm collimator and the common arm optical distributor, the to-be-detected object may be an eyeball, and one of the different focused areas to which the light is transmitted from the first sample arm collimator maycornea.

In the dual focusing optical coherence imaging system, the other of the different focused areas to which the light is transmitted from the first sample arm collimator may be retina.

In the dual focusing optical coherence imaging system, the detection unit may include: a detection collimator for allowing the interference signal selected by the optical switch to exit as parallel light; a detection grating for allowing the parallel light incident from the detection collimator to be diffracted; a detection lens for allowing the light diffracted by the detection grating to be focusingly transmitted; and a detector for converting the diffracted light incident from the detection lens into an electrical signal.

In the dual focusing optical coherence imaging system, the system may further include an optical isolator or an optical circulator disposed between the light source unit and the main optical distributor for allowing the light generated from the light source unit to be transmitted to only the main optical distributor.

In the dual focusing optical coherence imaging system, at least one of the optical distributors included in the main optical distributor and the interference unit may include an optical fiber distributor.

In the dual focusing optical coherence imaging system, the system may further include: control unit for receiving the electrical signal from the detection unit; storage unit connected to the control unit for storing preset data therein; a calculation unit for executing a calculation operation and calculating video information in response to a control signal generated from the control unit based on the electrical signal applied to the control unit from the detection unit and the preset data stored in the storage unit; and a display unit for displaying an image of the video information thereon in response to an image control signal from the control unit.

In the dual focusing optical coherence imaging system, the light source unit may include a wavelength-tunable light source.

In the dual focusing optical coherence imaging system, a part of the first interference part and the second interference part, and the common sample arm may constitute a hand-held probe.

In another aspect, the present invention provides a dual focusing optical coherence imaging system, including: a light source unit for generating broadband light; a main optical distributor for distributing the light generated from the light source to allow the light to be propagated; an interference unit including first and second interference parts for forming interference signals with respect to different focused areas of an object to be detected using the light distributed from the optical distributor, and a common sample arm commonly connected to the first and second interference parts for forming an optical path difference of the light irradiated onto different focused areas of the to-be-detected object from the first and second interference parts between the different focused areas; an optical switch connected to the first and second interference parts to select at least one of the interference signals transmitted from the first and second interference parts; and a detection unit for converting the interference signal selected by the optical switch according to a preset mode into an electrical signal.

In the dual focusing optical coherence imaging system, the first interference part may include: a first optical distributor for receiving the broadband light distributed from the main optical distributor; a first sample arm comprising a first sample arm collimator for receiving the light distributed from the first optical distributor; and a first reference arm comprising a first reference arm collimator for receiving the light distributed from the first optical distributor other than the light distributed to the first sample arm, and a first reference mirror for reflecting the light incident from the first reference arm collimator to allow the reflected light to return to the first optical distributor.

In the dual focusing optical coherence imaging system, the second interference part may include: a second optical distributor for receiving the broadband light distributed from the main optical distributor; a second sample arm comprising a second sample arm collimator for receiving the light distributed from the second optical distributor; and a second reference arm comprising a second reference arm collimator for receiving the light distributed from the second optical distributor other than the light distributed to the second sample arm, and a second reference mirror for reflecting the light incident from the second reference arm collimator to allow the reflected light to return to the second optical distributor.

In the dual focusing optical coherence imaging system, the first interference part may include: a first optical distributor for receiving the broadband light distributed from the main optical distributor; a first sample arm comprising a first sample arm collimator for receiving the light distributed from the first optical distributor; and a first reference arm comprising a first reference arm collimator for receiving the light distributed from the first optical distributor other than the light distributed to the first sample arm, and a first reference mirror for reflecting the light incident from the first reference arm collimator to allow the reflected light to return to the first optical distributor, the second interference part may include: a second optical distributor for receiving the broadband light distributed from the main optical distributor; a second sample arm comprising a second sample arm collimator for receiving the light distributed from the second optical distributor; and a second reference arm comprising a second reference arm collimator for receiving the light distributed from the second optical distributor other than the light distributed to the second sample arm, and a second reference mirror for reflecting the light incident from the second reference arm collimator to allow the reflected light to return to the second optical distributor, and the common sample arm may include: a common arm optical distributor for reflecting the light transmitted from the first optical distributor and the second optical distributor through the first sample arm collimator and the second sample arm collimator; a common arm optical scanner for irradiating the light reflected from the common arm optical distributor toward the different focused areas of the object to be detected; and a common arm optical path dispersion unit for irradiating the light irradiated from the common arm optical scanner onto the different focused areas of the to-be-detected object, and re-transmitting the light reflected from the different focused areas of the to-be-detected object to the common arm optical scanner, the common arm optical path dispersion unit being disposed between the to-be-detected object and the common arm optical scanner to form an optical path difference of the light irradiated onto different focused areas of the to-be-detected object from the first and second interference parts between the different focused areas.

In the dual focusing optical coherence imaging system, the common arm optical path dispersion unit may include: a first dispersion optical distributor for distributing the light irradiated from the optical scanner so as to allow a first sample optical path to be formed in the same direction as the propagating direction of the light irradiated from the optical scanner and allow a second sample optical path to be formed in a direction perpendicular to the propagating direction of the light irradiated from the optical scanner; a second dispersion optical distributor disposed between the first dispersion optical distributor and the to-be-detected object so as to confront the first dispersion optical distributor in such a manner as to be positioned on the first sample optical path and the second optical path; a dispersion objective lens disposed between the second dispersion optical distributor and the to-be-detected object so as to allow the light transmitted through the second dispersion optical distributor to be focused on different focused areas of the to-be-detected object and allow the light reflected from the to-be-detected object to be transmitted to the second dispersion optical distributor; a second dispersion sample optical path mirror disposed on the second sample optical path so as to allow the second sample optical path to be formed different from the first sample optical path; and a second dispersion sample optical path focusing lens disposed on a partial path of the second sample optical path, which does not intersect the first sample optical path.

In the dual focusing optical coherence imaging system, the second dispersion sample optical path focusing lens may be disposed between the first dispersion optical distributor and the second dispersion sample optical path mirror.

In the dual focusing optical coherence imaging system, the common arm optical path dispersion unit may include: a first dispersion optical distributor for distributing the light irradiated from the optical scanner so as to allow a first sample optical path to be formed in the same direction as the propagating direction of the light irradiated from the optical scanner and allow a second sample optical path to be formed in a direction perpendicular to the propagating direction of the light irradiated from the optical scanner; a second dispersion optical distributor disposed between the first dispersion optical distributor and the to-be-detected object so as to confront the first dispersion optical distributor in such a manner as to be positioned on the first sample optical path and the second optical path; a second dispersion sample optical path mirror disposed on the second sample optical path so as to allow the second sample optical path to be formed different from the first sample optical path; and a first dispersion sample optical path focusing lens disposed on a partial path of the first sample optical path, which does not intersect the second sample optical path so as to allow the light transmitted through the second dispersion optical distributor to focusingly irradiated onto a first focused area of the to-be-detected object; and a second dispersion sample optical path focusing lens disposed on a partial path of the second sample optical path, which does not intersect the first sample optical path so as to allow the light transmitted through the second dispersion optical distributor to focusingly irradiated onto a second focal area different from the first focused area of the to-be-detected object.

In the dual focusing optical coherence imaging system, the first reference arm may include a first reference optical path formed between the first reference arm collimator and the first reference mirror, and the second reference arm may include: a second reference optical path formed between the second reference arm collimator and the second reference mirror; and a common reference optical distributor through which the light on the first reference optical path and the light on the second reference optical path are passed commonly.

In the dual focusing optical coherence imaging system, the first reference arm may include: a first dispersion reference optical path optical distributor for transmitting light incident through the common reference optical distributors; a first dispersion reference optical path mirror for reflecting the light exiting the first dispersion reference optical path optical distributor; and a first dispersion reference optical path lens for allowing the light reflected from the first dispersion reference optical path mirror to be focused on the surface of the first reference mirror.

In the dual focusing optical coherence imaging system, the second reference arm may include: a second dispersion reference optical path optical distributor for transmitting light incident through the common reference optical distributors; a second dispersion reference optical path mirror for reflecting the light exiting the second dispersion reference optical path optical distributor; and a second dispersion reference optical path lens for allowing the light reflected from the second dispersion reference optical path mirror to be focused on the surface of the second reference mirror.

In the dual focusing optical coherence imaging system, the first interference part may include a first reference polarization controller provided between the first optical distributor and the first reference arm collimator, and the second interference part may include a second reference polarization controller provided between the second optical distributor and the second reference arm collimator.

In the dual focusing optical coherence imaging system, the optical switch may be connected to the first optical distributor and the second optical distributor to receive the interference signals from the first optical distributor and the second optical distributor for transmission to the detection unit, and may include a switching polarization controller disposed at an at least one position of positions between the optical switch and the first optical distributor/the second optical distributor and a position between the optical switch and the detection unit.

In the dual focusing optical coherence imaging system, the to-be-detected object may be an eyeball, and one of the different focused areas to which the light is transmitted from the first sample arm collimator may be a cornea.

In the dual focusing optical coherence imaging system, the other of the different focused areas to which the light is transmitted from the first sample arm collimator may be a retina.

In the dual focusing optical coherence imaging system, the detection unit may include: a detection collimator for allowing the interference signal selected by the optical switch to exit as parallel light; a detection grating for allowing the parallel light incident from the detection collimator to be diffracted; a detection lens for allowing the light diffracted by the detection grating to be focusingly transmitted; and a detector for converting the diffracted light incident from the detection lens into an electrical signal.

In the dual focusing optical coherence imaging system, the system may further include an optical isolator or an optical circulator disposed between the light source unit and the main optical distributor for allowing the light generated from the light source unit to be transmitted to only the main optical distributor.

In the dual focusing optical coherence imaging system, at least one of the optical distributors included in the main optical distributor and the interference unit may include an optical fiber distributor.

In the dual focusing optical coherence imaging system, the system may further include: a control unit for receiving the electrical signal from the detection unit; a storage unit connected to the control unit for storing preset data therein; a calculation unit for executing a calculation operation and calculating video information in response to a control signal generated from the control unit based on the electrical signal applied to the control unit from the detection unit and the preset data stored in the storage unit; and a display unit for displaying an image of the video information thereon in response to an image control signal from the control unit.

In the dual focusing optical coherence imaging system, the light source unit may include a wavelength-tunable light source.

In the dual focusing optical coherence imaging system, the detection unit may include a photodiode or photodetector for converting the interference signal selected by the optical switch into the electrical signal.

In the dual focusing optical coherence imaging system, a part of the first interference part and the second interference part, and the common sample arm may constitute a handheld probe.

In another aspect, the present invention provides a dual focusing optical coherence imaging system including: a light source unit for generating broadband light; a main optical distributor for distributing the light generated from the light source to allow the light to be propagated; an interference unit including first and second interference parts for forming interference signals with respect to different focused areas of an object to be detected using the light distributed from the optical distributor, and a common sample arm commonly connected to the first and second interference parts for forming an optical path difference of the light irradiated onto different focused areas of the to-be-detected object from the first and second interference parts between the different focused areas; a detection unit for converting the interference signal transmitted from the interference unit into an electrical signal, wherein the light source unit comprises a wavelength-tunable light source, and the detection unit comprises a photodiode or photodetector for converting the interference signal transmitted from the second interference unit into the electrical signal.

Advantageous Effects

The dual focusing optical coherence imaging system according to the present invention as constructed above have the following advantages.

First, the dual focusing optical coherence imaging system according to the present invention enables the simultaneous or alternative acquisition of the video information on the different focused areas of a single to-be-detected object through a single scan operation performed on the single to-be-detected object.

Second, the dual focusing optical coherence imaging system according to the present invention enables the simultaneous or alternative acquisition of the video information on the different focused areas of a retina and cornea of an eyeball as the to-be-detected object through a single scan operation.

Third, the dual focusing optical coherence imaging system according to the present invention enables the simultaneous or alternative acquisition of the images on the different focused areas of the to-be-detected object to acquire an interference signal for the to-be-detected object through a switching operation based on a sequential or preset manner by an optical switch, thereby achieving compactness and the manufacturing cost of the system.

Fourth, the dual focusing optical coherence imaging system according to the present invention enables the simultaneous or alternative acquisition of the images on the different focused areas of the to-be-detected object to acquire an interference signal for the to-be-detected object through a switching operation based on a sequential or preset manner by an optical switch, so that the number of the spectrometers can be reduced to a single number, thereby providing the effects of preventing distortion of the image signal, processing a trigger signal in a simple and easy manner, and minimizing the measurement time owing to unnecessity of a video signal calibration algorithm based on software/hardware.

Fifth, the dual focusing optical coherence imaging system according to the present invention enables the simultaneous measurement of the cornea and the retina through a sample arm by irradiating a focused light onto the cornea to measure the cornea through hardware-based technological modification of the system, and at the same time irradiating parallel light onto the eyeball to measure the retina, so that the simultaneous measurement of the cornea and the retina can be made by the sample arm, and the position of a reference mirror for measurement of the cornea and the position of a reference mirror for measurement of the retina are fixed separately using two optical fiber distributors (or fiber couplers), thereby simultaneously acquiring individual diagnosis video information on the cornea and the retina by controlling the travel distance of the light from an optical fiber distributor Sixth, the dual focusing optical coherence imaging system according to the present invention provides effects of enhancing a patient's convenience of diagnosis through the simultaneous measurement of the retina and cornea, reducing the medical costs, and shortening the diagnosis time.

Seventh, the dual focusing optical coherence imaging system according to the present invention includes a light source unit as a wavelength-tunable light source and a detection unit corresponding to the light source unit so that the interference part and the detection unit are directly interconnected or indirectly interconnected through the optical switch, to achieve the simultaneous, alternative, or sequential acquisition of the images on the different focused areas of the to-be-detected object, and the at the same time implement a compact structure, thereby reducing the manufacturing cost and improving utility of a space and portability/convenience owing to the compactness of the mounting space.

Eighth, the dual focusing optical coherence imaging system according to the present invention is configured to include a common sample arm that includes a common arm optical path dispersion unit and is connected to the first and second interference parts to form an optical path difference of the light irradiated onto different focused areas of the same to-be-detected object so that more accurate acquisition of video information on the different focused areas can be made by more accurate generation of the interference signal.

Ninth, the dual focusing optical coherence imaging system according to the present invention is configured to include a reference arm corresponding to the common arm optical path dispersion unit so as to allow an optical path of the sample arm side where the light irradiated onto the to-be-detected object is positioned to be correspondingly matched to an optical path of the reference arm side, thereby preventing or minimizing a possibility of a loss of optical information due to a difference between the elements on the optical path, and thus enabling more accurate acquisition of video information.

Tenth, the dual focusing optical coherence imaging system according to the present invention uses one of a vertical light component and a horizontal light component at one focal position of a single to-be-detected object and the other light component at the other focal position of the single to-be-detected object in imaging video information on a plurality of focal positions of the single to-be-detected object, thereby minimizing an optical loss, and thus maximizing the imaging efficiency at the plurality of focal positions of the single to-be-detected object.

BEST MODE FOR CARRYING OUT THE INVENTION

Now, preferred embodiments of a dual focusing optical coherence imaging system according to the present invention will be described hereinafter in detail with reference to the accompanying drawings.

Figure 1:
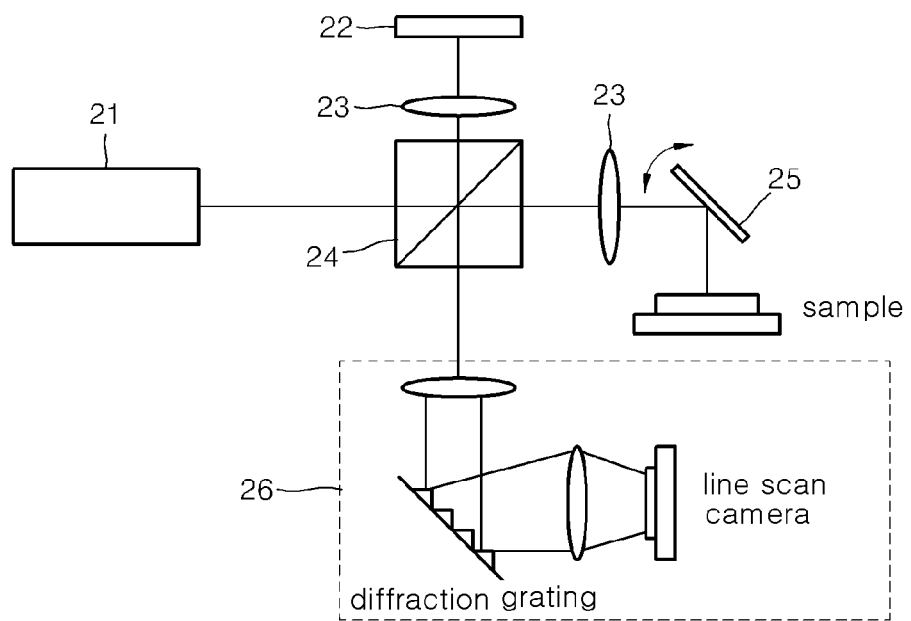
FIG. 1 is a basic schematic view illustrating an optical coherence tomography (SD-OCT) system according to the prior art.
Figure 2:
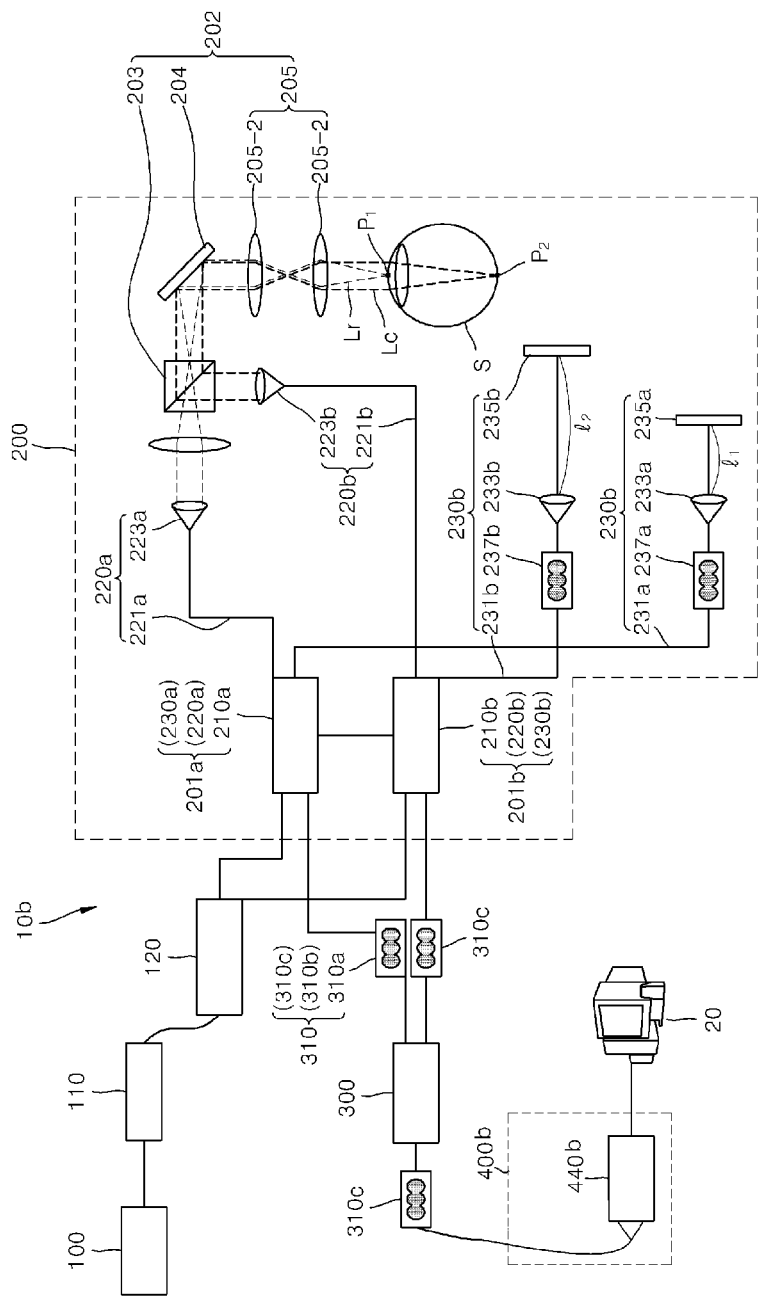
FIG. 2 is a schematic block diagrammatic view illustrating a dual focusing optical coherence imaging system according to one embodiment of the present invention.
Figure 3:
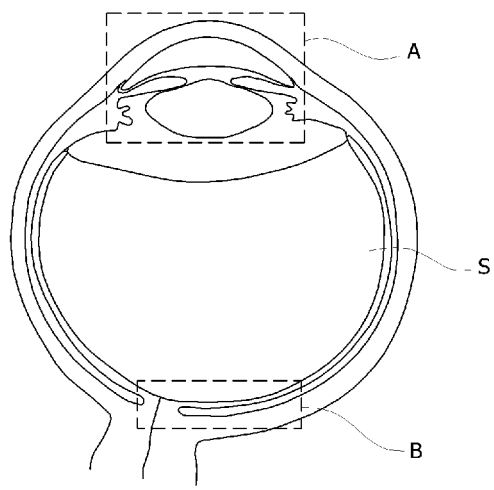
FIG. 3 is a schematic state view illustrating an eyeball as an object to be detected in a dual focusing optical coherence imaging system according to an embodiment of the present invention.
Figure 4:
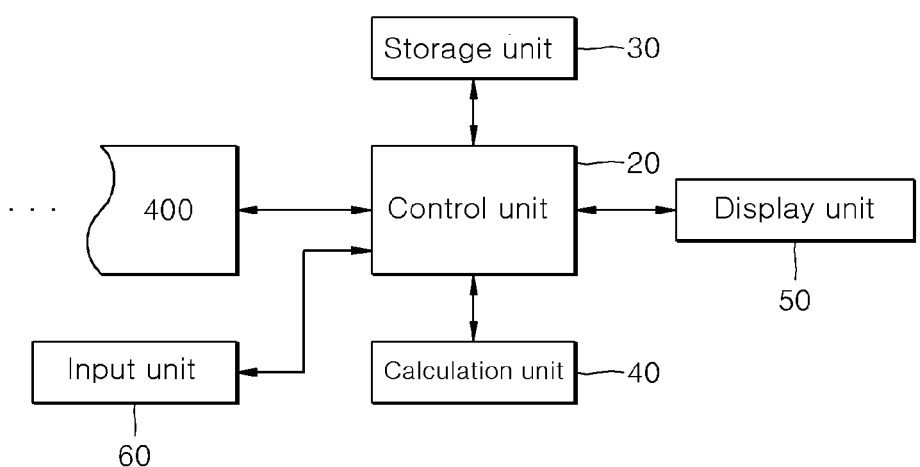
FIG. 4 is a schematic block diagrammatic view illustrating additional constituent elements of a dual focusing optical coherence imaging system according to an embodiment of the present invention.
Figure 5:
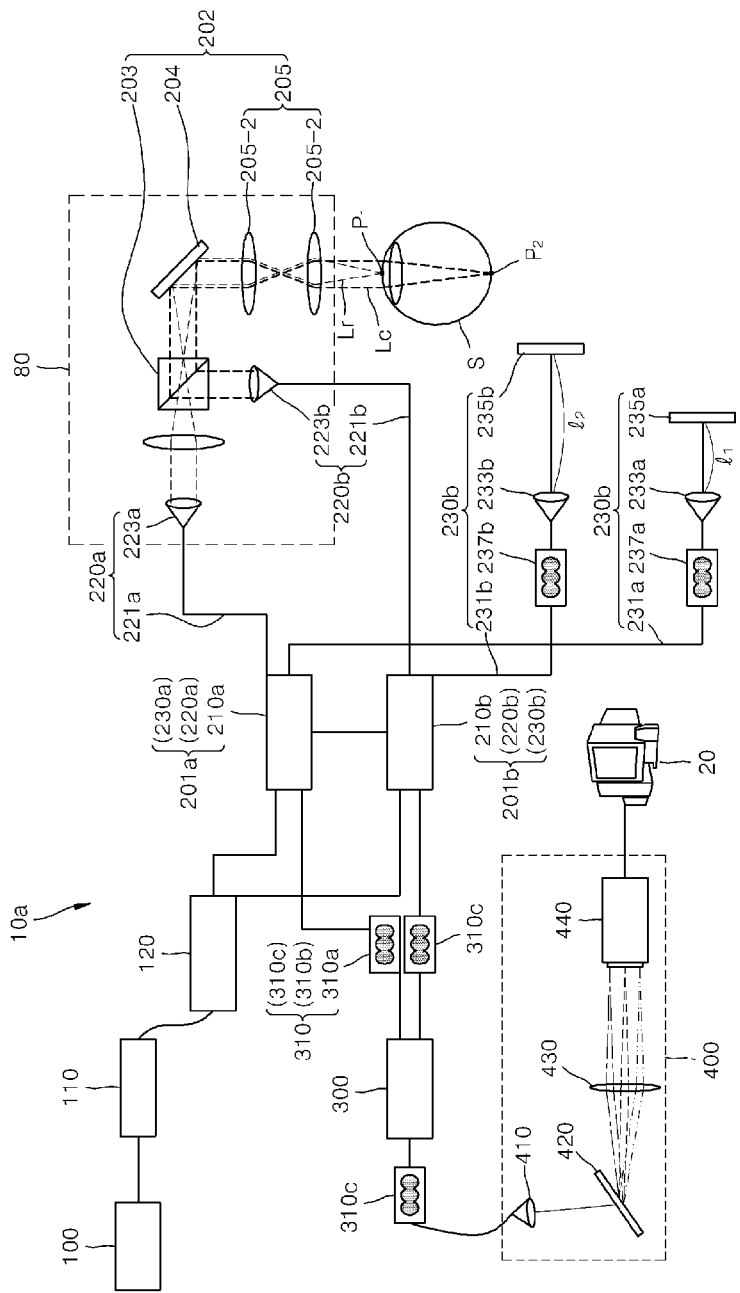
FIG. 5 is a schematic block diagrammatic view illustrating another example of a dual focusing optical coherence imaging system according to one embodiment of the present invention.
Figure 6:
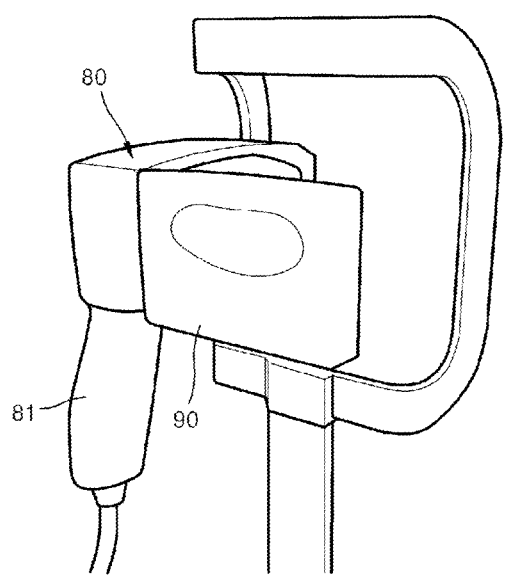
FIG. 6 is a schematic partial perspective view illustrating another example of a dual focusing optical coherence imaging system according to one embodiment of the present invention.

FIG. 1 is a basic schematic view illustrating an optical coherence tomography (SD-OCT) system according to the prior art, FIG. 2 is a schematic block diagrammatic view illustrating a dual focusing optical coherence imaging system according to one embodiment of the present invention, FIG. 3 is a schematic state view illustrating an eyeball as an object to be detected in a dual focusing optical coherence imaging system according to an embodiment of the present invention, FIG. 4 is a schematic block diagrammatic view illustrating additional constituent elements of a dual focusing optical coherence imaging system according to an embodiment of the present invention, FIG. 5 is a schematic block diagrammatic view illustrating another example of a dual focusing optical coherence imaging system according to one embodiment of the present invention, and FIG. 6 is a schematic partial perspective view illustrating another example of a dual focusing optical coherence imaging system according to one embodiment of the present invention.

Figure 7:
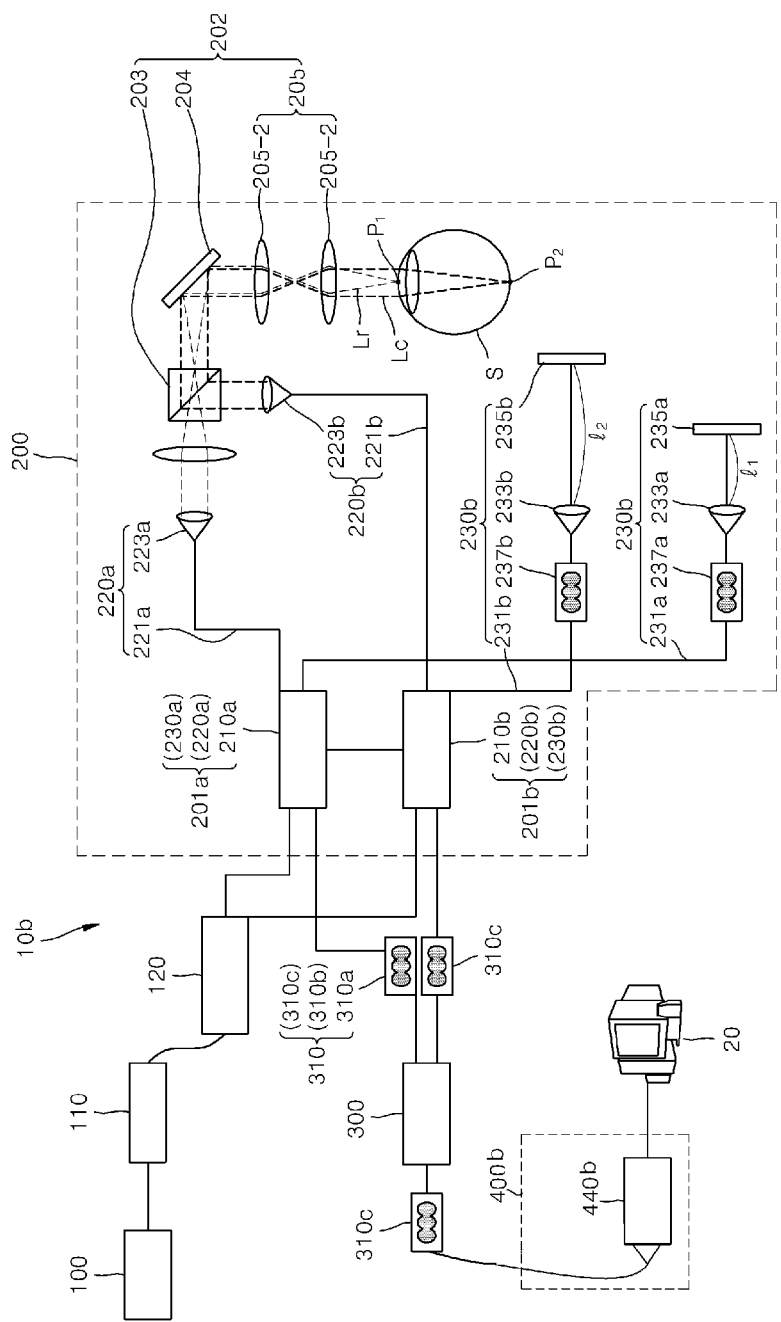
FIG. 7 is a schematic block diagrammatic view illustrating still another example of a dual focusing optical coherence imaging system according to one embodiment of the present invention.
Figure 8:
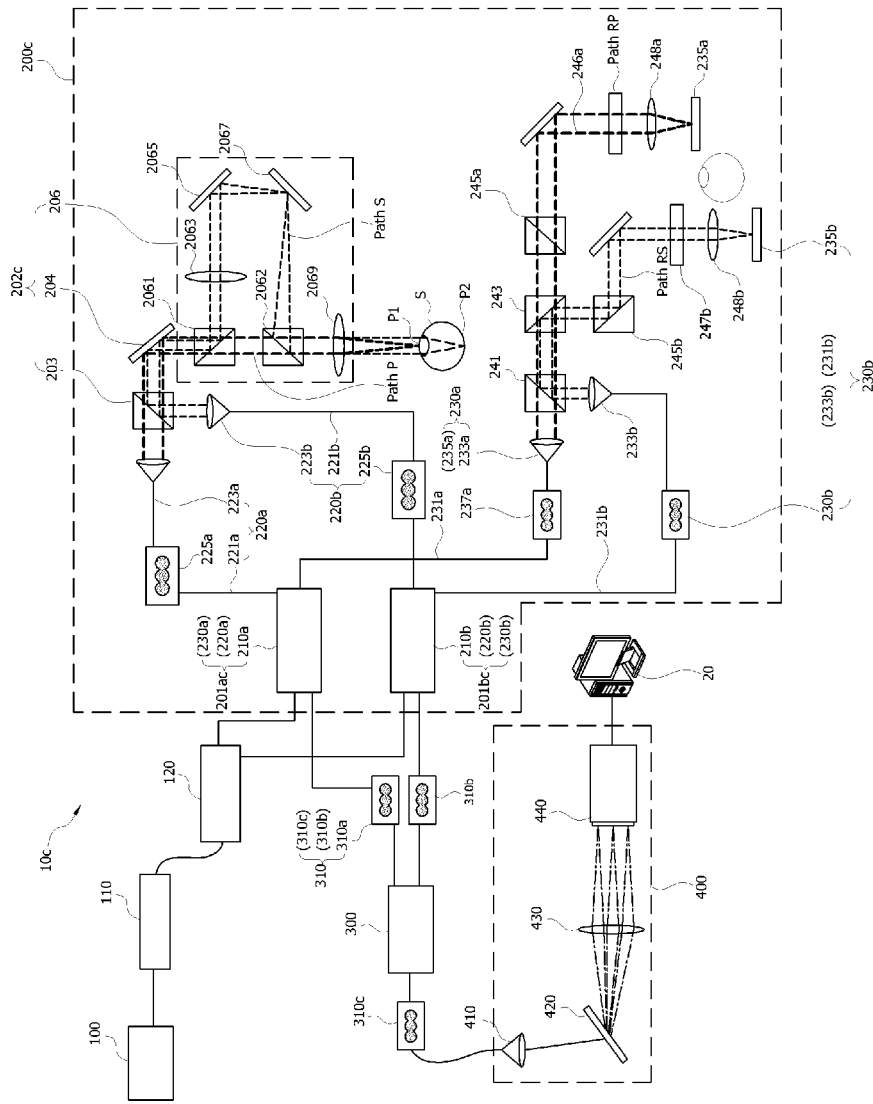
FIG. 8 is a schematic block diagrammatic view illustrating a dual focusing optical coherence imaging system according to another embodiment of the present invention.
Figure 9:
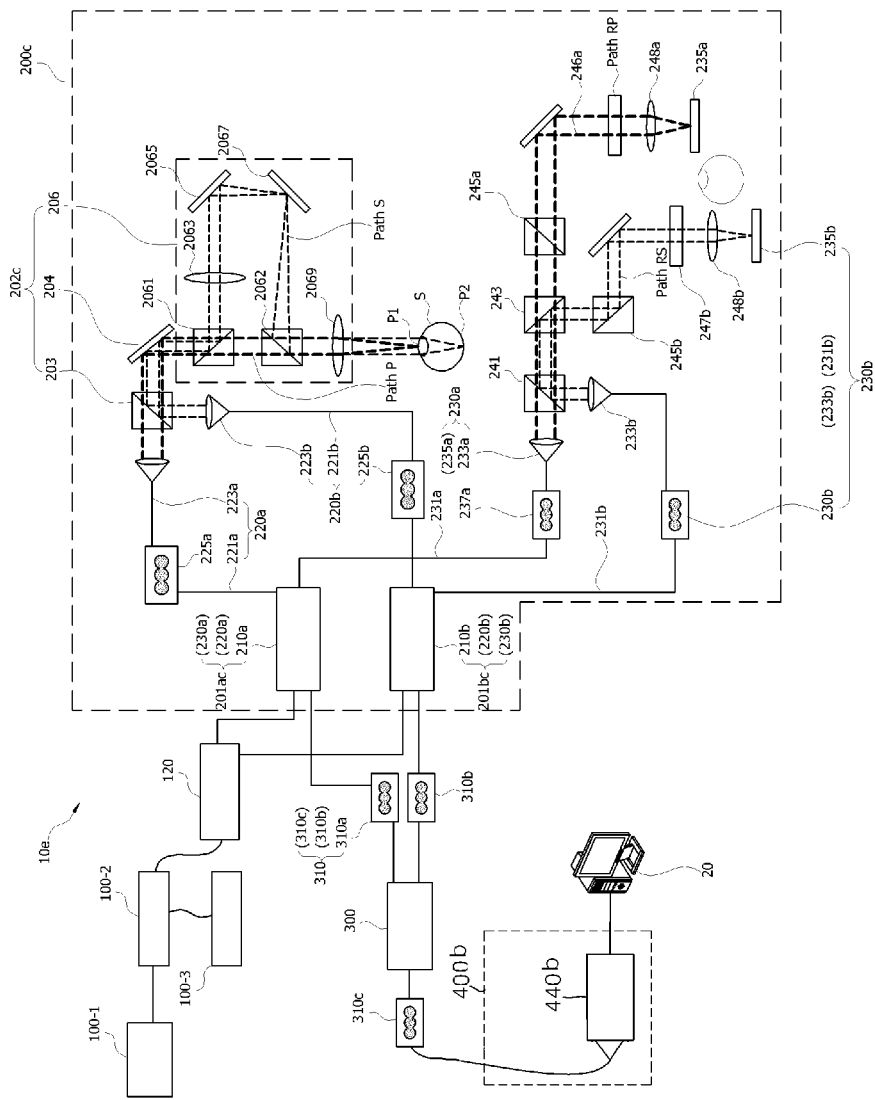
FIG. 9 is a schematic block diagrammatic view illustrating a modified example of a dual focusing optical coherence imaging system according to another embodiment of the present invention.
Figure 10:
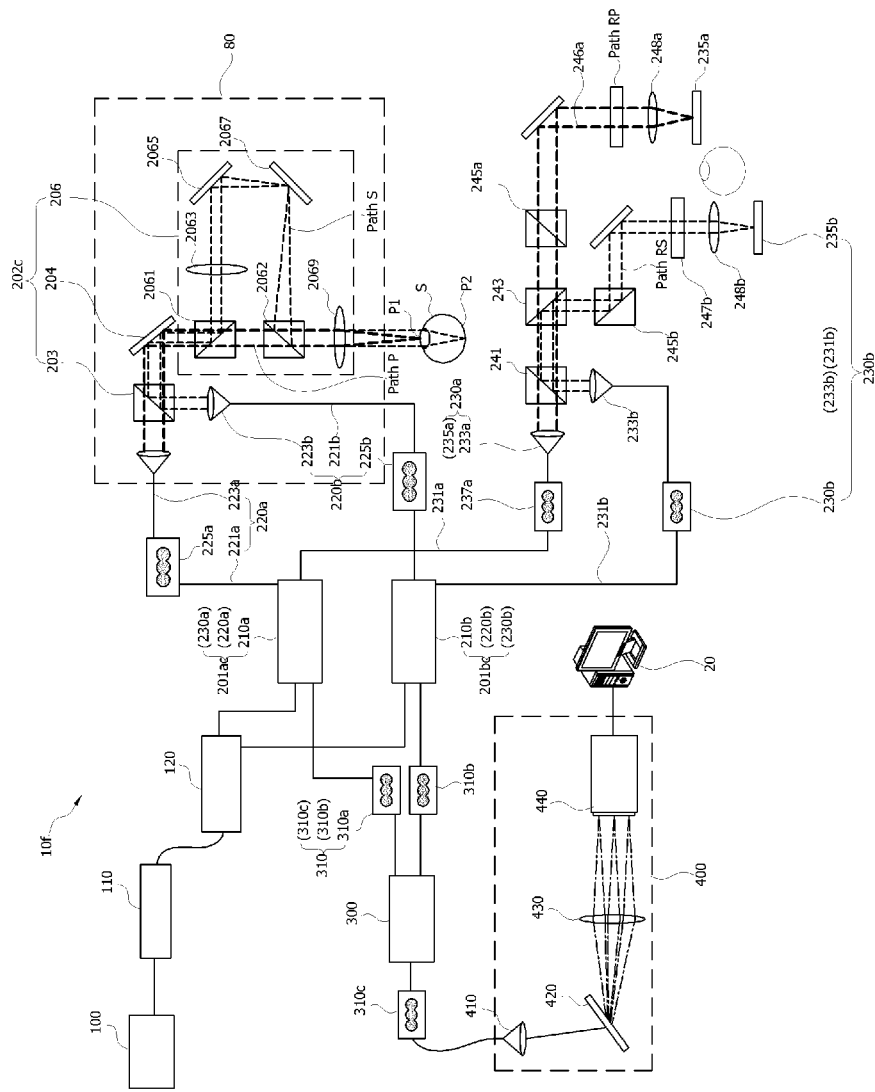
FIG. 10 is a schematic block diagrammatic view illustrating another modified example of a dual focusing optical coherence imaging system according to another embodiment of the present invention.
Figure 11:
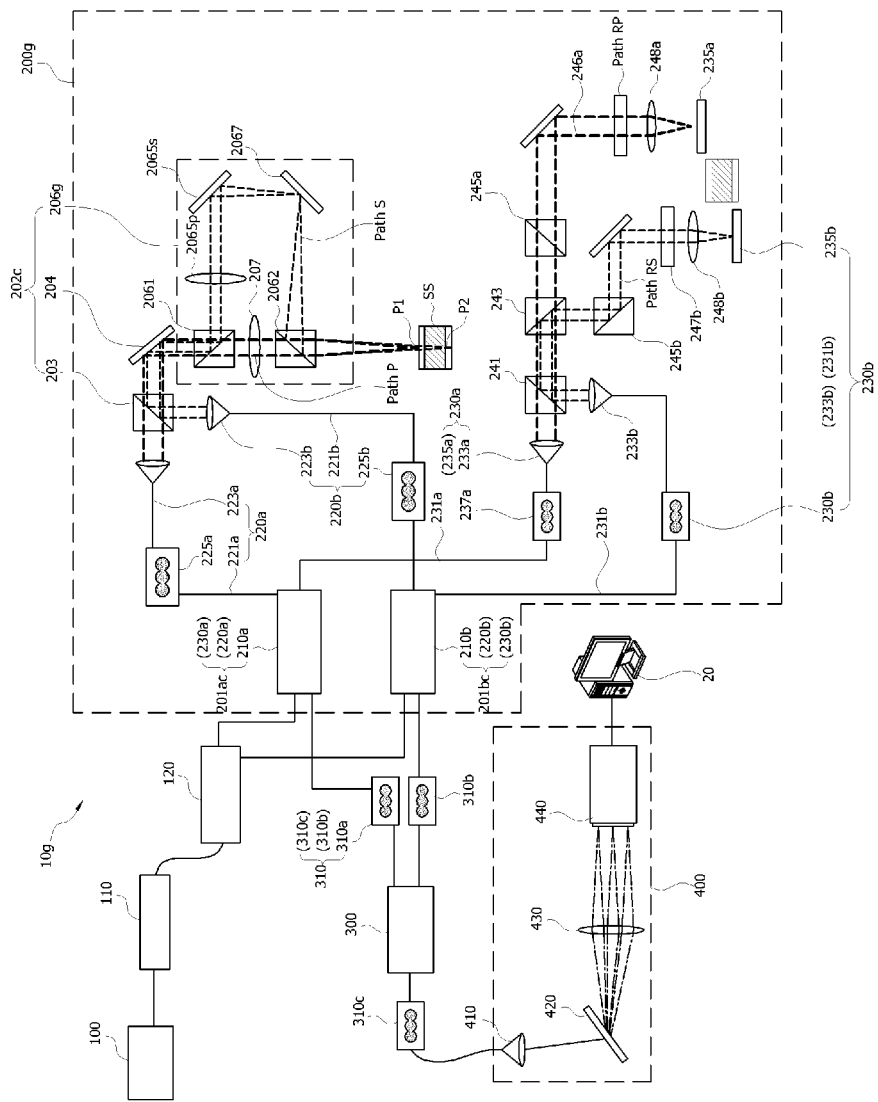
FIG. 11 is a schematic block diagrammatic view illustrating still another modified example of a dual focusing optical coherence imaging system according to another embodiment of the present invention.

FIG. 7 is a schematic block diagrammatic view illustrating still another example of a dual focusing optical coherence imaging system according to one embodiment of the present invention, FIG. 8 is a schematic block diagrammatic view illustrating a dual focusing optical coherence imaging system according to another embodiment of the present invention, FIG. 9 is a schematic block diagrammatic view illustrating a modified example of a dual focusing optical coherence imaging system according to another embodiment of the present invention, FIG. 10 is a schematic block diagrammatic view illustrating another modified example of a dual focusing optical coherence imaging system according to another embodiment of the present invention, and FIG. 11 is a schematic block diagrammatic view illustrating still another modified example of a dual focusing optical coherence imaging system according to another embodiment of the present invention.

A dual focusing optical coherence imaging system 10 according to an embodiment of the present invention includes a light source 100, an interference unit 200, an optical switch 300, and a detection unit 400.

The light source unit 100 generates broadband light, and includes a low-coherence light source in this embodiment. Hereinafter, the construction in which the dual focusing optical coherence imaging system 10 includes a light source unit including a low-coherence light source, and a detection unit as a spectroscopic unit including a line scan camera as a detector and performing a spectroscopic function will be described. In addition, the construction in which the dual focusing optical coherence imaging system 10 includes a light source unit employing a wavelength-tunable light source, particularly a high-speed, wavelength-tunable light source (swept source) among the low-coherence light sources, and a detection unit employing a photodiode or dual balance photodetector as a detector will be described hereinafter.

An average time interval during which a light wave reaching a point in an arbitrary space is vibrated predictably to maintain a sine function form without any phase change is called the "coherence time", which is a barometer of determining the temporal coherence of the light wave. When observed at a stationary point in a space, a propagating light wave is vibrated in a sine function form only during the time interval during which a phase is constantly maintained. At this time, a spatial distance of the light wave that is vibrated regularly until the phase is changed arbitrarily is called the "coherence length", which is used as a barometer for grasping a spectroscopically pure degree of the light wave. The low coherence light source is a light source in which the coherence length of the light wave is short, and includes a broad spectrum band. An optical transmission path between constituent elements for transmitting the broadband light generated from the light source unit 100 is implemented as an optical fiber.

The broadband light generated from the light source unit 100 is transmitted to a main optical distributor 120. In this embodiment, an optical isolator 110 is disposed between the main optical distributor 120 and the light source unit 100. The optical isolator 110 is an element that blocks light propagating in an opposite direction to the propagating direction of the light. In the process of transmitting the broadband light generated from the light source unit 100 to the main optical distributor 120, the transmission of the reflected light to the light source unit 100 can be interrupted to protect the light source unit 100. Although the optical isolator 110 is shown in this embodiment, various selections can be made within a range of executing a function that performs the transmission of light to a desired side but interrupts the transmission of light to a undesired side, such as including an optical circulator instead of the optical isolator.

The main optical distributor 120 distributes the broadband light transmitted thereto from the light source unit 100 for transmission to a first interference part 201a and a second interference part 201b, which will be described later. Although the distribution ratio of the light between the first interference part 201a and the second interference part 201b of the interference unit 200 by the main optical distributor 120 was set to an equivalent ratio to acquire images of a cornea and a retina as different focused areas, which will be described later, this is merely an embodiment of the present invention and various modifications can be made depending on the use purpose and the setting environment.

The light distributed while passing through the main optical distributor 120 is transmitted to respective interference parts 201a and 201b of the interference unit 200, and a common sample arm 202, and then is irradiated onto an object to be detected (also called "to-be-detected object"). Thereafter, interference signals formed by the first and second interference parts 201a and 201b after the light is reflected from the to-be-detected object are transmitted to the detection unit 400 through the optical switch 300, which will be described later.

The interference unit 200 includes a first interference part 201a and a second interference part 201b, and a common sample arm 202. The first interference part 201a and the second interference part 201b are the same sample arms, and are commonly connected to the common sample arm 202. That is, the first interference part 201a and the second interference part 201b include reference arms that are difference from each other, which will be described, respectively, to acquire video information on different focused areas of the same to-be-detected object, which are different from each other, and the interference unit 200 includes the common sample arm to form the different focused areas, so that individual video information can be acquired through the different focused areas of the same to-be-detected object.

The first interference part 201a includes a first optical distributor 210a, a first sample arm 220a, and a first reference arm 230a. The first optical distributor 210a receives the broadband light distributed from the main optical distributor 120 and re-distributes the received broadband light.

The first optical distributor 210a is connected to the first sample arm 220a and the first reference arm 230a. The re-distributed light is transmitted to the first sample arm 220a and the first reference arm 230a from the first optical distributor 210a.

The first sample arm 220a includes a first sample arm collimator 223a. The first sample arm collimator 223a is connected to the first optical distributor 210a through a first sample arm optical fiber 221a. The first sample arm collimator 223a receives the light distributed from the first optical distributor 210a to generate parallel light. The parallel light generated from the first sample arm collimator 223a is irradiated onto a focused area of the to-be-detected object S via the common sample arm 202.

The light distributed from the first optical distributor 210a is transmitted to the first reference arm 230a, which includes a first reference arm collimator 233a and a first reference mirror 235a. The first reference arm collimator 233a is connected to the first optical distributor 210a through a first reference arm optical fiber 231a. Such a first reference arm optical fiber 231a allows the equilibrium state between the first reference arm collimator 233a and the first reference mirror 235a, which will be described later, to be smoothly formed. In order to reduce the influence of the first reference arm optical fiber 231a on the light intensity, a first reference polarization controller 237a may be disposed between the first optical distributor 210a and the first reference arm collimator 233a. The first reference polarization controller 237a may allow the intensity profile of the light to be close to a Gaussian distribution while maximizing the light intensity of the broadband light emitted from the light source unit.

The first reference arm collimator 233a also receives the distributed broadband light from the first optical distributor 210a to generate parallel light in the same manner as that in the first sample arm collimator 231a. The parallel light exiting the first reference arm collimator 233a is irradiated onto the first reference mirror 235a. The irradiated parallel light is reflected from the first reference mirror 235a and then returns to the first optical distributor 210a via the first reference arm collimator 233a. The light returned to the first optical distributor 210a meets the light for a first focused area P1 of the to-be-detected object S, which is reflected from the to-be-detected object S via the first sample arm 220a and then the common sample arm 202, and returns to the first optical distributor 210a to cause an interference phenomenon to form an interference signal for acquiring an image of the first focused area of the to-be-detected object.

The second interference part 201b also has the same structure as that of the first interference part 201a. That is, the second interference part 201b includes: a second optical distributor 210b that receives the broadband light distributed from the main optical distributor 120; a second sample arm 220b including a second sample arm collimator 223b that receives the light distributed from the second optical distributor 210b; and a second reference arm 230b including a second reference arm collimator 233b that receives the light distributed from the second optical distributor 210b other than the light distributed to the second sample arm 220b, and a second reference mirror 235b that reflects the light incident from the second reference arm collimator 233b to allow the reflected light to return to the second optical distributor 210b.

The structure of the second interference part 201b in which the second sample arm 220b and the second reference arm 230b are connected to each other by means of a second sample arm optical fiber 221b and a second reference arm optical fiber 231b is the same as that of the first interference part 201a. But the first interference part 201a and the second interference part 201b has the structure for acquiring image signals for the different focused areas P1 and P2 of the same to-be-detected object S. The distance l1 between the first reference arm collimator 233a and the first reference mirror 235a of the first interference part 201a is different from the distance l2 between the second reference arm collimator 233b and the second reference mirror 235b of the second interference part 201b (l1≠l2). In addition, the second interference part 201b may include a second reference polarization controller 237b provided between the second optical distributor 210b and the second reference arm collimator 233b similarly to the first interference part 201a.

The main optical distributor, the first optical distributor, the second optical distributor as mentioned above may be implemented as an optical fiber distributor (or a fiber coupler) to achieve the stable and constant distribution and output of the light irrespective of the incident angle of light and a simple and compact structure.

The common sample arm 202 includes a common arm optical distributor 203, a common arm optical scanner 204, and a common arm objective lens 205. The common arm optical distributor 203 reflects the light transmitted from the first optical distributor and the second optical distributor through the first sample arm collimator 223a and the second sample arm collimator 223b to allow the reflected light to be transmitted to the common arm optical scanner 204. The common arm optical scanner 204 may be implemented as a galvanometer structure in which a mirror is mounted on a galvanometer and is rotated at the preset angle and speed. The light having passed through the common arm optical scanner 204 is irradiated onto the to-be-detected object S, more specifically onto the different focused areas P1 and P2 of the to-be-detected object S through the common arm objective lens 205. In this embodiment, the common arm objective lens 205 includes two objective lenses, i.e., a first objective lens 205-1 and a second objective lens 205-2. The number and type of the common arm objective lens is not limited thereto, and the common arm objective lens may be constructed in various manners depending on the relationship between the design specification and the focused areas of the to-be-detected object as a measurement target.

Thus, the broadband light respectively distributed through the first interference part 201a and the second interference part 201b via the main optical distributor 120 is transmitted to the first sample arm 220a/the second sample arm 220b and the first reference arm 230a/the second reference arm 230b via the first optical distributor 210a/the second optical distributor 210b. The light having passed the first sample arm 220a and the second sample arm 220b is transmitted to the common sample arm 202 to allow the transmitted light to be irradiated onto the different focused areas P1 and P2 of the to-be-detected object P. Thereafter, the light reflected from the different focused areas P1 and P2 to enable acquisition of an image signal for the focused areas P1 and P2 returns to the first optical distributor 210a and the second optical distributor 210b via the common sample arm 202 and the first sample arm 220a/the second sample arm 220b in the propagating direction opposite to that of the light incident on the different focused areas P1 and P2. At the same time, the light distributed from the first optical distributor 210a and the second optical distributor 210b and then transmitted to the first reference arm 230a and the second reference arm 230b is reflected from the first reference mirror 235a and the second reference mirror 235b, respectively, to allow the reflected light to return the first optical distributor 210a and the second optical distributor 210b through an reverse path. Thus, interference signals are generated due to an interference phenomenon between the light reflected from the different focused areas P1 and P2 to enable acquisition of images for the different focused areas P1 and P2 of the to-be-detected object S via the first sample arm 220a/the second sample arm 220b and the common sample arm 202, and the light reflected from the first reference mirror 235a and the second reference mirror 235b via the first reference arm 230a and the second reference arm 230b.

Meanwhile, in this embodiment, the common sample arm 202 further include a first sample arm focusing lens 207 provided between the first sample arm collimator 233a and the common arm optical distributor 203. The first sample arm focusing lens 207 can allow the light to be accurately transmitted to the first focused area P1. By virtue of the above construction, the light incident via the first sample arm 220a of the first interference part 201a forms a predetermined optical path so that the incident light is accurately focused on and irradiated onto the first focused area P1 of the to-be-detected object S via the common sample arm 202. In addition, the light incident via the second sample arm 220b of the second interference part 201b forms an optical path different from the optical path formed by the light incident via the first sample arm 220a so that the incident light is accurately focused on and irradiated onto the second focused area P2 of the to-be-detected object S, but not the first focused area P1 via the common sample arm 202. Although it has been described in this embodiment that the first sample arm focusing lens 207 is provided, various modifications can be made depending on the design specification and the inspection condition, such as having the structure in which the second sample arm focusing lens is disposed between the second sample arm and the common sample arm. The to-be-detected object S according to this embodiment is an eyeball, and the focused areas P1 and P2 are indicated by a cornea and a retina, respectively. In this embodiment, the first focused area P1 on which the light transmitted from the first sample arm collimator 223a of the first interference part 201a is irradiated is set to the cornea. In FIG. 3, there is shown a schematic state view illustrating an eyeball S as the to-be-detected object. When the focused area is formed at a region indicated by a reference symbol A, video information on the cornea and/or the crystalline lens can be acquired whereas when the focused area is formed at a region indicated by a reference symbol B, video information on the retina and/or the choroid can be acquired.

In FIG. 2, the respective segments indicated by reference symbols Lr and Lc are optical paths of the light transmitted and reflected through the first and second interference parts. The optical path indicated by the reference symbol Lr means an optical path of the light passing through the first interference part 201a, and the optical path indicated by the reference symbol Lc means an optical path of the light passing through the second interference part 201b. As shown in FIG. 2, the light incident on the eyeball as the to-be-detected object S through the first interference part 201a is focused on the cornea as the first focused area P1, and the light reflected from the cornea as the first focused area P1 takes a reverse path and meets the light reflected from the first reference arm 230a at the first optical distributor 210a to cause an interference phenomenon to form an interference signal for enabling acquisition of the image for the first focused area P1 of the to-be-detected object S. In addition, the light incident on the eyeball as the to-be-detected object S through the second interference part 201b is focused on the retina as the second focused area P2 by the crystalline lens present in the eyeball, and the light reflected from the retina as the second focused area P2 takes a reverse path and meets the light reflected from the first reference arm 230a at the first optical distributor 210a to cause an interference phenomenon to form an interference signal for enabling acquisition of the image for the second focused area P2 of the to-be-detected object S. Although it has been described in this embodiment that the first focused area is set to the cornea and the second focused area is set to the retina, the first focused area and the second focused area may be configured at various positions depending on the use environment and the purpose by controlling the first reference arm/the second reference arm and/or the common arm objective lens and/or the sample arm focusing lens.

The interference signals formed at the first optical distributor 210a and the second optical distributor 210b are transmitted to the optical switch 300, which is connected to the first optical distributor 210a and the second optical distributor 210b. The optical switch 300 performs a switching operation to sequentially transmit light as interference signals, i.e., an interferenced light, i.e., an interference signal with respect to the first focused area P1 through the first interference part 201a, and an interference light, i.e., an interference signal with respect to the second focused area P2 through the second interference part 201b to the detection unit 400, which will be described later.

The optical switch 300 employs a high-speed optical switch for a broad bandwidth of 800 nm in this embodiment. The optical switch 300 may perform a selective operation in response to a control signal to make various selections, such as achieving a simultaneous imaging of the first focused area and the second focused area, i.e., the cornea and the retina, a single imaging of the cornea as the first focused area, or a single imaging of the retina as the second focused area.

In the meantime, at least one switching polarization controllers 310; 310a, 310b, and 310c may be disposed in front of and/or at the rear of the optical switch 300. That is, in this embodiment, the switching polarization controllers 310; 310a, 310b, and 310c is constructed such that it is disposed between the optical switch 300 and the first optical distributor 210a, between optical switch 300 and the second optical distributor, and between the optical switch 300 and the detection unit 400. The switching polarization controllers 310; 310a, 310b, and 310c enables the stable transmission of the interference signals to minimize a loss of the intensity of the interference signals being transmitted.

The detection unit 400 converts the interference signal transmitted from the optical switch 300 into an electrical signal. In this embodiment, the detection unit 400 is implemented as a spectroscopic unit, but in the case where the light source unit is implemented as a wavelength-tunable light source as described below, the detection unit may be constructed in various manners within a range of converting the interference signals into electrical signals, such as including a detector like a photodiode or dual-balanced photodetector of a compact structure.

The detection unit 400 implemented as a spectroscopic unit includes a detection collimator 410, a detection grating 420, a detection lens 430, and a detector 440. The detection collimator 410 converts at least one interference signal selected by and transmitted from the optical switch 300 into parallel light, which is in turn transmitted to the detection grating 420.

The detection grating 420 allows the interference signal as the incident parallel light to be diffracted. In this embodiment, the detection grating 420 employs a transmission grating with 1200 grooves/mm, but may be constructed in various manners depending on a design specification.

The parallel light diffracted by the detection grating 420 is transmitted to the detector 440 through the detection lens 430. In this embodiment, the detector 440 is implemented as a line scan camera with a scan rate of 70000 lines/s, but in the case where the light source unit is implemented as a wavelength-tunable light source as described below, the detector of the detection unit may be constructed in various manners depending on a design specification, such as being implemented as a photodiode or dual-balanced photodetector of a compact structure, and may be modified in various manners depending on design specification within a range of including a detection function of converting the optical interference signal into electrical signal.

The electrical signal converted from the interference signal by the detection unit 400 is transmitted to the control unit 20. In this process, the electrical signal is converted into a digital signal. The dual focusing optical coherence imaging system 10 of the present invention includes a control unit 20, a storage unit 30, a calculation unit 40, and a display unit 50 as shown in FIGS. 2 and 4. The control unit 20 is electrically connected to the storage unit 30 and the calculation unit. The storage unit 30 can store preset data including preset image coversion data needed to the electrical signal from the detection unit 400 into an image signal. The calculation unit 40 executes a predetermined calculation process, i.e., an calculation process such as the Inverse Fast Fourier Transform (IFFT) and/or the k-domain calibration on the vertical and horizontal components of the digitally converted signal applied from the detection unit in response to a calculation control signal generated from the control unit 20. The control unit 20 can control the display unit 50 to in real-time display an image of video information thereon under the control of an image control signal therefrom using the preset image coversion data pre-stored in the storage unit 30 based on a result of the calculation.

In the meantime, the preset data may include preset mode data for a mode for switching the optical switch. That is, the dual focusing optical coherence imaging system 10 of the present invention further include an input unit 60, so that an input signal containing a user's intention can be inputted through the input unit 60 by the user. The preset mode can be displayed as an image on the display unit 30 through the preset mode data previously stored in the storage unit 30. When a selection is made by the user through the input unit 60, a selected input signal is applied to the control unit 20. Then, the control unit 20 controls the optical switch 300 to allow video information on a desired focused area of the to-be-detected object to be acquired so as to display an image of the video information on the display unit 50.

Also, in the meantime, although it has been described in the above-mentioned embodiment that the dual focusing optical coherence imaging system of the present invention is implemented as an integral system, it is not limited thereto and may be modified in various manners. That is, as shown in FIG. 5, another example of the dual focusing optical coherence imaging system 10*a* according to the present invention may further include a hand-held probe 80. In other words, the hand-held probe 80 may be constructed to include a part of the first interference part 201*a* and the second interference part 201*b*, and the common sample arm 202. The first sample arm collimator 223*a* of the first interference part 201*a*, the second sample arm collimator 223*b* of the second interference part 201*b*, and the common sample arm 202 may have the structure of being stably built in a probe body 81 (see FIG. 6), and the respective constituent elements of the hand-held probe 80 may have the structure of being connected to the first optical distributor and the second optical distributor through the optical fiber. By virtue of the above construction of the hand-held probe 80, the dual focusing optical coherence imaging system may be constructed such that a subject to be examined can be observed smoothly even in a state of not being seated.

In addition, it is apparent that such a hand-held probe 80 may include a probe display 90 to enhance a user's convenience (see FIG. 6).

Video information on the regions indicated by the reference symbols A and B in FIG. 3 can be acquired through the above dual focusing optical coherence imaging system. The optical switch may be switched sequentially so that video information on the retina and the cornea can be acquired simultaneously through a single scan operation. In addition, the optical switch may be maintained in a certain mode so that video information on specific focused areas, i.e., the video information on the cornea can be acquired and the video information on the retina can be acquired. As such, the dual focusing optical coherence imaging system of the present invention can execute various selective diagnosis functions of performing the simultaneous or alternative acquisition of the video information on the different focused areas of a single to-be-detected object through a single scan operation performed on the single to-be-detected object.

Also, in the meantime, in the above embodiment, a low coherence light source was used as the light source unit, but the present invention is not limited thereto and may include a wavelength-tunable light source as the light source unit. As shown in FIG. 7, still another example of the dual focusing optical coherence imaging system 10*b* according to one embodiment of the present invention includes a light source unit 100*b* including a wavelength-tunable light source. The light source unit 100*b* is an optical amplifier employing a gain mechanism in a semiconductor active layer such as semiconductor laser, and may be implemented as a semiconductor optical amplifier (SOA) that converts electric energy supplied from a power supply (not shown) into light. The light source unit 100*b* implemented as a semiconductor optical amplifier (SOA) has a broad bandwidth of 800 nm. In the case where the wavelength-tunable light source is used as the light source unit, the detection unit may be implemented as a simple structure. That is, as shown in FIG. 7, the detection unit 400*b* may have a simple structure of including a detector 440*b* that directly receives light of an interference signal outputted from the switching polarization controller 310*c* and converts the interference signal into an electrical signal. The detector 440*b* may be implemented as a photodiode or dual balanced photodetector.

By virtue of such a structure of the detection unit 400*b*, a complicated structure of the spectroscopic unit is excluded and a simple and compact structure can be achieved. This can improve implementability of a mobile imaging system through the operative cooperation between the spectroscopic unit and the above-mentioned hand-held probe.

Meanwhile, although it has been described in the above embodiment that the dual focusing optical coherence imaging system is constructed such that only the focused areas of the to-be-detected object are different from each other in the common sample arm and the substantially same optical path is formed, the dual focusing optical coherence imaging system of the present invention may have a structure that can improve the quality of the acquired image by achieving a structure in which the light for acquiring the images for different focused areas has optical paths that are different from each other. That is, an optical path difference is formed and a structure may be provided in which formation of a distribution difference in the sample arms is prevented in the interference process through the corresponding structure between the sample arms and the reference arms to minimize an optical loss, thereby improving the quality of the images for the different focused areas.

FIG. 8 shows a dual focusing optical coherence imaging system according to another embodiment of the present invention. To avoid a redundant description, like or same reference numerals in the above embodiment are given to corresponding element or parts of this embodiment, and the same constitution will be replaced with the constitution in the above embodiment.

A dual focusing optical coherence imaging system 10*c* according to another embodiment of the present invention includes a light source 100, an interference unit 200*c*, an optical switch 300, and a detection unit 400.

The light source unit 100 generates broadband light, and includes a low-coherence light source in this embodiment. As mentioned above, the low coherence light source is a light source in which the coherence length of the light wave is short, and includes a broad spectrum band. An optical transmission path between constituent elements for transmitting the broadband light generated from the light source unit 100 is implemented as an optical fiber.

The broadband light generated from the light source unit 100 is transmitted to a main optical distributor 120. In this embodiment, an optical isolator 110 is disposed between the main optical distributor 120 and the light source unit 100, so that the transmission of the reflected light to the light source unit 100 can be interrupted to protect the light source unit 100 in the process of transmitting the broadband light generated from the light source unit 100 to the main optical distributor 120.

The main optical distributor 120 distributes the broadband light transmitted thereto from the light source unit 100 for transmission to a first interference part 201*ac* and a second interference part 201*bc*, which will be described later.

Although the distribution ratio of the light between the first interference part 201*ac* and the second interference part 201*bc* of the interference unit 200 by the main optical distributor 120 was set to an equivalent ratio to acquire images of a cornea and a retina as different focused areas, which will be described later, in this embodiment, this is merely an embodiment of the present invention and various modifications can be made depending on the use purpose and the setting environment.

The light distributed while passing through the main optical distributor 120 is transmitted to respective interference parts 201*ac* and 201*bc* of the interference unit 200*c*, and a common sample arm 202*c*, and then is irradiated onto a to-be-detected object. Thereafter, interference signals formed by the first and second interference parts 201*ac* and 201*bc* after the light is reflected from the to-be-detected object are transmitted to the detection unit 400 through the optical switch 300, which will be described later. The interference unit 200*c* includes a first interference part 201*ac* and a second interference part 201*bc*, and a common sample arm 202*c*. The first interference part 201*ac* and the second interference part 201*bc* are commonly connected to the common sample arm 202*c*, and an optical path difference of the light irradiated onto different focused areas of the to-be-detected object from the first and second interference parts 201*ac* and 201*bc* between the different focused areas is formed at the common sample arm 202*c*. That is, the first interference part 201*a* and the second interference part 201*b* include reference arms that are difference from each other at least partly with respect to the respective interference parts, which will be described, respectively, to acquire video information on different focused areas of the same to-be-detected object, which are different from each other, and the interference unit 200*c* is constructed to include the common sample arm that is common but forms an optical path difference therein to form the different focused areas, so that individual video information having enhanced image quality can be acquired through the different focused areas of the same to-be-detected object.

The first interference part 201*ac* includes a first optical distributor 210*ac*, a first sample arm 220*a*, and a first reference arm 230*a*. The first optical distributor 210*a* receives the broadband light distributed from the main optical distributor 120 and re-distributes the received broadband light. The first optical distributor 210*a* is connected to the first sample arm 220*a* and the first reference arm 230*a*. The re-distributed light is transmitted to the first sample arm 220*a* and the first reference arm 230*a* from the first optical distributor 210*a*.

The first sample arm 220*a* includes a first sample arm collimator 223*a*. The first sample arm collimator 223*a* is connected to the first optical distributor 210*a* through a first sample arm optical fiber 221*a*. The first sample arm collimator 223*a* receives the light distributed from the first optical distributor 210*a* to generate parallel light. The parallel light generated from the first sample arm collimator 223*a* is irradiated onto a focused area of the to-be-detected object S via the common sample arm 202*c*.

The light distributed from the first optical distributor 210*a* is transmitted to the first reference arm 230*a*, which includes a first reference arm collimator 233*a* and a first reference mirror 235*a*. The first reference arm collimator 233*a* is connected to the first optical distributor 210*a* through a first reference arm optical fiber 231*a*. In order to reduce the influence of the first reference arm optical fiber 231*a* on the light intensity, a first reference polarization controller 237*a* may be disposed between the first optical distributor 210*a* and the first reference arm collimator 233*a*. The first reference polarization controller 237*a* may allow the intensity profile of the light to be close to a Gaussian distribution while maximizing the light intensity of the broadband light emitted from the light source unit, and can maximize the intensity of the interference signal through the control of polarization, thereby greatly improving the quality of images formed accordingly.

The first reference arm collimator 233*a* also receives the distributed broadband light from the first optical distributor 210*a* to generate parallel light in the same manner as that in the first sample arm collimator 231*a*. The parallel light exiting the first reference arm collimator 233*a* is irradiated onto the first reference mirror 235*a*.

The irradiated parallel light is reflected from the first reference mirror 235*a* and then returns to the first optical distributor 210*a* via the first reference arm collimator 233*a*. The light returned to the first optical distributor 210*a* meets the light for a first focused area P1 of the to-be-detected object S, which is reflected from the to-be-detected object S via the first sample arm 220*a* and then the common sample arm 202, and returns to the first optical distributor 210*a* to cause an interference phenomenon to form an interference signal for acquiring an image of the first focused area of the to-be-detected object.

The second interference part 201*bc* also has the same structure as that of the first interference part 201*ac*. That is, the second interference part 201*b* includes: a second optical distributor 210*b* that receives the broadband light distributed from the main optical distributor 120; a second sample arm 220*b* including a second sample arm collimator 223*b* that receives the light distributed from the second optical distributor 210*b*; and a second reference arm 230*b* including a second reference arm collimator 233*b* that receives the light distributed from the second optical distributor 210*b* other than the light distributed to the second sample arm 220*b*, and a second reference mirror 235*b* that reflects the light incident from the second reference arm collimator 233b to allow the reflected light to return to the second optical distributor 210b.

The structure of the second interference part 201bc in which the second sample arm 220b and the second reference arm 230b are connected to each other by means of a second sample arm optical fiber 221b and a second reference arm optical fiber 231b is the same as that of the first interference part 201ac. But the first interference part 201ac and the second interference part 201bc has the structure for acquiring image signals for the different focused areas P1 and P2 of the same to-be-detected object S. The distance l1 between the first reference arm collimator 233a and the first reference mirror 235a of the first interference part 201a is different from the distance l2 between the second reference arm collimator 233b and the second reference mirror 235b of the second interference part 201b, and a first reference optical path (PathRP) and a second reference optical path (PathRS) corresponding to a first sample optical path (PathP) and a second sample optical path (PathS) are formed in order to improve the quality of images.

That is, the first reference arm has a construction in which it is disposed correspondingly to match to the construction of the common sample arm to prevent deterioration of the quality of optical images due to an optical path difference between the first reference arm and the common sample arm. A first reference optical path formed by the first reference arm and a second reference optical path formed by the second reference arm partly share the same optical path, and thus the first reference arm includes common reference optical distributors 241 and 243 through which respective lights on the first reference optical path and the second reference optical path to pass commonly. As shown in FIG. 8, the first reference optical path is formed between the first reference arm collimator 233a and the first reference mirror 235a, and the second reference optical path is formed between the first reference arm collimator 233b and the second reference mirror 235b. The common reference optical distributors 241 and 243 are disposed between the first reference arm collimator 233a and the first reference mirror 235a and between the first reference arm collimator 233b and the second reference mirror 235b, i.e., on the first reference optical path and the second reference optical path so that respective lights can pass through the common reference optical distributors 241 and 243 commonly. The common reference optical distributors 241 and 243 correspond to a common arm optical distributor 203 and a first dispersion optical distributor 2061 of a common arm optical path dispersion unit 206, which will be described later. The number of the common reference optical distributors 241 and 243 provided is two. The common reference optical distributor 241 collects the respective lights transmitted from the first reference arm collimator 233a and the second reference arm collimator 233b and transmits the collected lights to the common reference optical distributor 243, which in turn distributes the transmitted light for transmission to the first reference mirror 235a and the second reference mirror 235b. On the contrary, the lights reflected from the first reference mirror 235a and the second reference mirror 235b travel along a reverse path and are transmitted to the common reference optical distributor 243, which in turn collects the transmitted lights for transmission to the common reference optical distributor 241. The reflected light incident on the common reference optical distributor 241 is transmitted to the first optical distributor 210a and the second optical distributor 210b via the first reference arm collimator 233a and the second reference arm collimator 233b.

In addition, other constituent elements disposed on the first reference optical path and the second reference optical path may be disposed between the common reference optical distributors 241 and 243 and the first reference mirror 253a and the second reference mirror 245b so that the first reference optical path and the second reference optical path form a structure of being matched to the first sample optical path and the second sample optical path of the common sample arm.

The first reference arm 230a includes a first dispersion reference optical path optical distributor 245a, a first dispersion reference optical path mirror 246a, and a first dispersion reference optical path lens 248a. The first dispersion reference optical path optical distributor 245a transmits light incident through the common reference optical distributors 241 and 243, and the first dispersion reference optical path mirror 246a reflects the light exiting the first dispersion reference optical path optical distributor 245a, and the first dispersion reference optical path lens 248a allows the light reflected from the first dispersion reference optical path mirror 246a to be focused on the surface of the first reference mirror 237a to minimize the dispersion of the light. The first dispersion reference optical path lens 248a may be implemented as an achromatic lens, and a first dispersion reference optical path filter 247a as a neutral density (ND) filter for adjusting the quantity of light may be provided between the first dispersion reference optical path lens 248a and the first dispersion reference optical path mirror 246a.

The second reference arm 230b includes a second dispersion reference optical path optical distributor 245b, a second dispersion reference optical path mirror 246b, and a second dispersion reference optical path lens 248b.

The second dispersion reference optical path optical distributor 245b transmits the light incident through the common reference optical distributors 241 and 243, the second dispersion reference optical path mirror 246b reflects the light exiting the second dispersion reference optical path optical distributor 245b and transmits the reflected light, and the second dispersion reference optical path lens 248b allows the light reflected from the second dispersion reference optical path mirror 246a to be focused on the surface of the second reference mirror 237b to minimize the dispersion of the light. The second dispersion reference optical path lens 248b may be implemented as an achromatic lens, and a second dispersion reference optical path filter 247b as a neutral density (ND) filter for adjusting the quantity of light may be provided between the second dispersion reference optical path lens 248b and the second dispersion reference optical path mirror 246b.

Herein, the common reference optical distributors 241 and 243 and the first dispersion reference optical path optical distributor 245a and the second dispersion reference optical path optical distributor 245b are implemented as a polarized beam splitter (PBS). The light forming the first reference optical path and the second reference optical path via the common reference optical distributors 241 and 243 is selected alternatively to match to a polarization structure of the common sample arm such that it is not overlapped with a horizontal light LP and a vertical light LS that are polarized, respectively.

That is, in this embodiment, the second reference arm has a structure in which the light on the first reference optical path is formed as the horizontal light LP and the light on the second reference optical path is formed as the vertical light LS so that a component other than a polarized component of each light is excluded on a corresponding reference optical path. The first dispersion reference optical path optical distributor 245a is disposed in parallel with an arrangement segment formed by the common reference optical distributors 241 and 243. In addition, the second dispersion reference optical path optical distributor 245b is disposed perpendicular to the arrangement segment formed by the common reference optical distributors 241 and 243, so that the horizontal light LP is used as the light on the first reference optical path and the vertical light LS is used as the light on the second reference optical path. This is merely an example, and it is apparent that the horizontal light LP and the vertical light LS are respectively used as the light on the first and second reference optical paths, and vice versa.

The light incident to the common reference optical distributor 241 from the first reference arm collimator 233a is transmitted to the common reference optical distributor 241, and only a component of the horizontal light LP of the light incident on the common reference optical distributor 241 from the first reference arm collimator 233a is transmitted through the common reference optical distributor 241, and then is transmitted to the first reference mirror 235a through the common reference optical distributor 243 and the first dispersion reference optical path optical distributor 245a to allow the transmitted light to be reflected from the first reference mirror 235a. Thereafter, the light reflected from the first reference mirror 235a is reflected from the first dispersion reference optical path mirror 246a via the first dispersion reference optical path lens 248a and the first dispersion reference optical path filter 247a, and then is sequentially transmitted to the common reference optical distributors 243 and 241 in this order via the first dispersion reference optical path optical distributor 245a. Then, the light transmitted to the common reference optical distributors 243 and 241 is transmitted to the first optical distributor 210a via the first reference arm collimator 233a and meets the light reflected from the first sample arm side to cause an optical interference phenomenon. That is, only a component of the horizontal light LP can be used by properly controlling the common reference optical distributors 241 and 243 and the first dispersion reference optical path optical distributor 245a on the first reference optical path.

In addition, the light is incident on the common reference optical distributor 241 from the second reference arm collimator 233b, and only a component of the vertical light LS of the light incident to the common reference optical distributor 241 from the second reference arm collimator 233b is transmitted to the second reference mirror 235b via the common reference optical distributor 243 and the second dispersion reference optical path optical distributor 245b. Thereafter, the light transmitted to the second reference mirror 235b is reflected from the second reference mirror 235b and is reflected from the second dispersion reference optical path mirror 246b via the second dispersion reference optical path lens 248b and the second dispersion reference optical path filter 247b. Then, the light reflected from the second dispersion reference optical path mirror 246b is transmitted to and reflected from the second dispersion reference optical path optical distributor 245b. Thereafter, the light reflected from the second dispersion reference optical path optical distributor 245b is sequentially transmitted to the common reference optical distributors 243 and 241 in this order, and is transmitted to the second optical distributor 210b via the second reference arm collimator 233b. The light transmitted to the second optical distributor 210b meets the light reflected from the second sample arm side to cause an optical interference phenomenon. That is, only a component of the vertical light LS can be used by properly controlling the common reference optical distributors 241 and 243 and the second dispersion reference optical path optical distributor 245b on the second reference optical path.

Further, the second interference part 201bc may also include a second reference polarization controller 237a disposed between the second optical distributor 210b and the second reference arm collimator 233b as in the first interference part 201ac.

The main optical distributor, the first optical distributor, and the second optical distributor as mentioned above may be implemented as an optical fiber distributor (or a fiber coupler) to achieve the stable and constant distribution and output of the light irrespective of the incident angle of light and a simple and compact structure.

The common sample arm 202c includes a common arm optical distributor 203, a common arm optical scanner 204, and a common arm objective lens 205. The common arm optical distributor 203 reflects the light transmitted from the first optical distributor and the second optical distributor through the first sample arm collimator 223a and the second sample arm collimator 223b to allow the reflected light to be transmitted to the common arm optical scanner 204.

In this case, the respective lights incident on the common arm optical distributor 203 through the first sample arm collimator 223a and the second sample arm collimator 223b are selected alternatively such that only a component of one light is not overlapped with a component selected with respect to the other light. That is, only a component of the horizontal light LP of the light incident on the common arm optical distributor 203 from the first sample arm collimator 223a is transmitted through the common arm optical distributor 203 and then is transmitted to common arm optical scanner 204. In addition, only a component of the vertical light LS of the light incident on the common arm optical distributor 203 from the second sample arm collimator 223b is reflected from the common arm optical distributor 203, and then is transmitted to the common arm optical scanner 204. By virtue of the above structure of the common sample arm, an optical path difference of the light forming the images of different focused areas of the to-be-detected object is formed through the optical path optical distributor implemented as an PBS disposed within the common arm optical path dispersion unit 206 so that video information on the to-be-detected object can be acquired more accurately.

The common arm optical scanner 204 may be implemented as a galvanometer structure in which a mirror is mounted on a galvanometer and is rotated at the preset angle and speed. The light having passed through the common arm optical scanner 204 is irradiated onto the to-be-detected object S, more specifically onto the different focused areas P1 and P2 of the to-be-detected object S through the common arm optical path dispersion unit 206. The light incident on the common arm optical path dispersion unit 206 forms different optical paths, i.e., a first sample optical path and a second sample optical path depending on whether the incident light is polarized as a horizontal light component or a vertical light component.

The first sample optical path and the second sample optical path are indicated with the dotted lines denoted by reference symbols PathP and PathS in the drawing. The horizontal light component LP forming the first sample optical path PathP is transmitted to a first dispersion optical distributor 2061 and a second dispersion optical distributor 2062, which are implemented as a PBS. In addition, the vertical light component LS forming the second sample optical path PathS has a structure in which the light is reflected and transmitted on the optical path.

More specifically, the common arm optical path dispersion unit 206 includes a first dispersion optical distributor 2061, a second dispersion optical distributor 2062, a dispersion objective lens 2069, second dispersion sample optical path mirrors 2065 and 2067, and a second dispersion sample optical path focusing lens 2063. The first dispersion optical distributor 2061 and the second dispersion optical distributor 2062 are implemented as a PBS as mentioned above.

The first dispersion optical distributor 2061 and the second dispersion optical distributor 2062 form different optical paths depending on whether the light is a polarized component. That is, an optical path is determined depending on whether the light polarized in the common optical distributor 203 and passed through the common arm optical scanner 204 is the horizontal light component LP or the vertical light component LS. The first dispersion optical distributor 2061 splits the light to be irradiated onto the to-be-detected object from the optical scanner 204, and forms the first sample optical path PathP formed in the same direction as the propagating direction of the light to be irradiated onto the to-be-detected object from the optical scanner 204, and the second sample optical path PathS formed in a direction perpendicular to the propagating direction of the light to be irradiated onto the to-be-detected object from the optical scanner 204. The second dispersion optical distributor 2062 is disposed between the first dispersion optical distributor 2061 and the to-be-detected object so as to confront the first dispersion optical distributor 2061, and is positioned on the first sample optical path PathP and the second sample optical path PathS, so that the first sample optical path PathP and the second sample optical path PathS pass through the first and second dispersion optical distributors 2061 and 2062.

The second dispersion sample optical path mirrors 2065 and 2067 are disposed on the second sample optical path PathS to form the second sample optical path PathS such that the lights splited from the first dispersion optical distributor 2061 join in the second dispersion optical distributor 2062. In the case where the light is reflected from the to-be-detected object and is propagated in an opposite direction to the direction in which the light is irradiated onto the to-be-detected object, the second dispersion sample optical path mirrors 2065 and 2067 can transmit a vertical light component splitted and reflected from second dispersion optical distributor to the first dispersion optical distributor 2061. The second sample optical path PathS is formed different from the first sample optical path PathP. In this embodiment, two second dispersion sample optical path mirrors 2065 and 2067 are provided but this is merely one example and the present invention is not limited thereto.

The dispersion objective lens 2069 is disposed between the second dispersion optical distributor 2062 and the to-be-detected object S. The dispersion objective lens 2069 allows the lights transmitted through and reflected from the second dispersion optical distributor 2062 to be respectively irradiated into different focused areas of the to-be-detected object S, and allows the light reflected from the different focused areas P1 and P2 of the to-be-detected object S to be transmitted to the second dispersion optical distributor 2062.

In addition, the second dispersion sample optical path focusing lens 2063 is disposed on the second sample optical path PathP between the first dispersion optical distributor 2061 and the second dispersion sample optical path mirror 2065. The reason for this is because dispersion objective lens 2069 is disposed between the to-be-detected object S and the second dispersion optical distributor 2061 in this embodiment so as to allow light to be accurately focused on a second focused area P2 through the second dispersion sample optical path focusing lens 2063. That is, in this embodiment, the dispersion objective lens 2069 is disposed on the first sample optical path PathP and the second sample optical path PathS1. In the case where the to-be-detected object S is an eyeball, the crystalline lens of the eyeball acts as anther lens. The light on the first sample optical path PathP, which has passed through the dispersion objective lens 2069, is accurately focused on the first focused area P1 as the cornea, and the light on the second sample optical path PathS, which has passed through the second dispersion sample optical path focusing lens 2063, is converted into parallel light through the dispersion objective lens 2069 so as to be irradiated onto the eyeball as the to-be-detected object S. The crystalline lens of the eyeball functions as a separate lens so that the vertical light component of the second sample optical path PathS is focusingly irradiated onto the retina as a second focal position Ps of the to-be-detected object S to enable accurate acquisition of an image of the focused area of the to-be-detected object S.

That is, by virtue of the above common arm optical path dispersion unit 206, the horizontal light component LP having passed the first sample arm collimator 223a and the common arm optical distributor 203 is transmitted to the first and second dispersion optical distributors 2061 and 2062 along the first sample optical path PathP, and then is transmitted to the first focused area P1 of the to-be-detected object S through the dispersion objective lens 2069 and is reflected from the first focused area P1 of the to-be-detected object S. Thereafter, the reflected light is transmitted to the first sample arm collimator 223a along a reverse path, and then the first optical distributor so that it meets the light reflected from the first reference arm side to generate an interference signal.

In addition, the vertical light component LS having passed the second sample arm collimator 223b and the common arm optical distributor 203 is reflected from the first dispersion optical distributor 2061 and is transmitted along the second sample optical path PathS. Then, the light reflected from the first dispersion optical distributor 2061 is transmitted to the second dispersion optical distributor 2062 via the second dispersion sample optical path focusing lens 2063 and the second dispersion sample optical path mirrors 2065 and 2067, and then is reflected from the second dispersion optical distributor 2062 to allow the reflected light to be transmitted to the to-be-detected object S via the dispersion objective lens 2069. At this time, a parallel light is incident on the to-be-detected object S via the second dispersion sample optical path focusing lens 2063 and the dispersion objective lens 2069 and is focused on the retina as a second focused area P2 through the crystalline lens of the to-be-detected object S as an eyeball. Thereafter, the light focused on the retina is reflected from the retina and is re-transmitted to the second sample arm collimator 223b and then the second optical distributor along the reverse path so that the re-transmitted light meets the light reflected from the second reference arm side to generate an interference signal.

By virtue of the common sample arm 202c including the common arm optical path dispersion unit 206, the first interference part 201ac, second interference part 201bc, it is possible to generate interference signals for more accurately acquiring video information on the different focused areas P1 and P2 of the to-be-detected object S.

The to-be-detected object S according to this embodiment may be an eyeball similarly to the aforementioned embodiment, and the different focused areas P1 and P2 may be indicated with the cornea and the retina. If the fact that the video information acquired for the different focused areas P1 and P2 is improved in the image quality is added, the video information is the same as that described in the aforementioned embodiment.

Besides, the interference signals formed in the first optical distributor 210a and the second optical distributor 210b are transmitted to the optical switch 300, which is connected to the first optical distributor 210a and the second optical distributor 210b. The optical switch 300 performs a switching operation to sequentially transmit light as interference signals, i.e., an interferenced light, i.e., an interference signal with respect to the first focused area P1 through the first interference part 201ac, and an interference light, i.e., an interference signal with respect to the second focused area P2 through the second interference part 201bc to the detection unit 400, which will be described later.

In addition, the optical switch 300 employs a high-speed optical switch for a broad bandwidth of 800 nm in this embodiment as described above. The optical switch 300 may perform a selective operation in response to a control signal to make various selections, such as achieving a simultaneous imaging of the first focused area and the second focused area, i.e., the cornea and the retina, a single imaging of the cornea as the first focused area, or a single imaging of the retina as the second focused area.

The detection unit 400 converts the interference signal transmitted from the optical switch 300 into an electrical signal. In this embodiment, the detection unit 400 is implemented as a spectroscopic unit, The detection unit 400 implemented as a spectroscopic unit is includes a detection collimator 410, a detection grating 420, a detection lens 430, and a detector 440. The detection collimator 410 converts at least one interference signal selected by and transmitted from the optical switch 300 into parallel light, which is in turn transmitted to the detection grating 420. The detection grating 420 allows the interference signal as the incident parallel light to be diffracted. In this embodiment, the detection grating 420 employs a transmission grating with 1800 grooves/mm, but may be constructed in various manners depending on a design specification. The parallel light diffracted by the detection grating 420 is transmitted to the detector 440 through the detection lens 430.

In this embodiment, the detector 440 is implemented as a line scan camera with a scan rate of 70000 lines/s, but in the case where the light source unit is implemented as a wavelength-tunable light source as described below as shown in FIG. 9, the detector of the detection unit may be constructed in various manners depending on a design specification, such as being implemented as a photodiode or dual-balanced photodetector of a compact structure, and may be modified in various manners depending on design specification within a range of including a detection function of converting the optical interference signal into electrical signal. That is, as show in FIG. 9, a light source unit 100-1 of a dual focusing optical coherence imaging system 10e may include a wavelength-tunable light source, and the light source unit 100-1 implemented as the wavelength-tunable light source is connected to a trigger coupler 100-2. The trigger coupler 100-2 can be connected to a trigger interferometer 100-3 to perform a predetermined trigger operation.

In addition, the detection unit may be implemented as a structure of including a detector such as a compact photodiode or dual balanced photodetector. As shown in FIG. 9, the detector 440b is implemented as the photodiode or dual balance photodetector connected to the optical switch 300 and/or the switching polarization controller 310c. Although the system according to this embodiment includes the construction in which the detector 440b is provided in single number and the optical switch is provided between the detector and the first optical distributor/the second optical distributor to perform a switching operation to acquire individual video information, the present invention is not limited thereto and may have a structure in which a separate detector is provided and is directly connected to the first optical distributor 210a and the second optical distributor 210b as well as to the control unit 20 so that interference information on different focused areas P1 and P2 of the to-be-detected object can be acquired separately or simultaneously.

The electrical signal converted from the interference signal by the detection unit 400 is transmitted to the control unit 20 in the same manner as that in the aforementioned embodiment. In this process, the electrical signal is converted into a digital signal. As shown in FIGS. 2 and 4, the dual focusing optical coherence imaging system 10 of the present invention includes a control unit 20, a storage unit 30, a calculation unit 40, and a display unit 50. The function of each of the elements is the same as that in the aforementioned embodiment.

In addition, the dual focusing optical coherence imaging system 10f according to the present invention may further include a hand-held probe 80 (see FIGS. 6 and 10) in the same manner as in the aforementioned embodiment. In other words, the hand-held probe 80 of the dual focusing optical coherence imaging system 10f may be constructed to include a part of the first interference part 201ac and the second interference part 201bc, and the common sample arm 202c. The first sample arm collimator 223a of the first interference part 201ac, the second sample arm collimator 223b of the second interference part 201bc, and the common sample arm 202c may have the structure of being stably built in a probe body 81 (see FIG. 6), and the respective constituent elements of the hand-held probe 80 may have the structure of being connected to the first optical distributor and the second optical distributor through the optical fiber. By virtue of the above construction of the hand-held probe 80, the dual focusing optical coherence imaging system may be constructed such that a subject to be examined can be observed smoothly even in a state of not being seated.

In addition, it is apparent that such a hand-held probe 80 may include a probe display 90 to enhance a user's convenience.

Although it has been described in the above embodiment that an example of the to-be-detected object S is taken as an eyeball and examples of the different focused areas are taken as a cornea and a retina, the to-be-detected object of the present invention as a target for acquisition of interference video information on different focused areas thereof is not limited to the eyeball. That is, the to-be-detected object may be other bodily regions besides the eyeball, and may be applied to various fields depending on the needs, such as being taken as an object other than bodily regions.

That is, as shown in FIG. 11, a dual focusing optical coherence imaging system 10g may be provided which enables acquisition of images for different focused areas of the same to-be-detected object other than the eyeball. The dual focusing optical coherence imaging system 10g is substantially the same as that in the aforementioned embodiments except a partial construction of the common arm optical path dispersion unit of the common sample arm.

Thus, like same reference numerals in the above embodiment are given to corresponding element or parts of this embodiment, and the same constitution will be replaced with the constitution in the above embodiment and a description will be made centering on a difference from the aforementioned embodiments to avoid a redundant description.

In the aforementioned embodiments, in the case where the to-be-detected object S is an eyeball, the crystalline lens included in the eyeball acts as a lens. Thus, the light irradiated onto the retina must be transmitted as parallel light to the to-be-detected object S as the eyeball so as to set the focused areas as the cornea and the retina. To this end, the system according to this embodiment is constructed to further include a second sample optical path focusing lens disposed between the first sample optical path and the second sample optical path so as to as parallel light form one of the lights passing through a dispersion objective lens through which a horizontal light and a vertical light pass commonly. But in the case where the to-be-detected object SS is not the eyeball, the crystalline lens is excluded so that the focal points on the first sample optical path and the second sample optical path can be controlled through a separate lens. Namely, as shown in FIG. 11, although a common arm optical path dispersion unit 206g includes a first dispersion optical distributor 2061, a second dispersion optical distributor 2062, and second dispersion sample optical path mirrors 2065 and 2067 and the arrangement structure thereof is the same as that in the aforementioned embodiments, the common arm optical path dispersion unit 206g may have a structure in which the dispersion objective lens is excluded and the to-be-detected object SS directly confront the second dispersion optical distributor 2062. A first dispersion sample optical path focusing lens 2065P and a second dispersion sample optical path focusing lens 2065S may disposed on respective optical paths so that the parallel light on the first sample optical path PathP and the second sample optical path PathS is focused on the different focused areas of the to-be-detected object to achieve an accurate acquisition of images of the different focused areas. In this embodiment, a first dispersion sample optical path focusing lens 2065P is disposed between a first dispersion optical distributor 2061 and a second dispersion optical distributor 2062, and a second dispersion sample optical path focusing lens 2065S is disposed between a first dispersion optical distributor 2061 and second dispersion sample optical path mirrors 2065 and 2067. This arrangement position of the first dispersion sample optical path focusing lens 2065P and the second dispersion sample optical path focusing lens 2065S may be modified depending the design specification. By virtue of above structure, images of different focused areas of the to-be-detected object SS can be acquired more accurately. In addition, the light source unit and the detector shown in FIG. 11 may be implemented as a light source unit including a wavelength-tunable light source and a detector like a photodiode, and may be modified in various manners, such as having a structure in which the light source and the detector are directly interconnected or indirectly interconnected through the optical switch as in the aforementioned embodiments.

The above embodiments are merely of illustrative purpose to describe the present invention and not intended to limit the scope of the invention. That is, various modifications can be made within a range of having a structure in which dual focused areas of a single to-be-detected object can be formed, and images of two focused areas of the single to-be-detected object can be acquired through a single scan operation such that an image for a desired focused area is acquired by switching the optical switch or dual images for different focused areas are acquired simultaneously through a separate signal.

INDUSTRIAL APPLICABILITY

The dual focusing optical coherence imaging system according to the present invention can be used as an ophthalmic diagnosis system for diagnosing an eyeball as a to-be-detected object as well as can be used a medical implement and other inspection equipment that can simultaneously acquire video information on different focused areas of a corresponding to-be-detected object as a bodily region or an object other than the eyeball.

While the present invention has been described in connection with the exemplary embodiments illustrated in the drawings, they are merely illustrative and the invention is not limited to these embodiments. It will be appreciated by a person having an ordinary skill in the art that various equivalent modifications and variations of the embodiments can be made without departing from the spirit and scope of the present invention. Therefore, the true technical scope of the present invention should be defined by the technical spirit of the appended claims.

The invention claimed is:

1. A dual focusing optical coherence imaging system comprising:
   a light source unit for generating broadband light;
   a main optical distributor for distributing the light generated from the light source to allow the light to be propagated;
   an interference unit including first and second interference parts for forming interference signals with respect to different focused areas of an object to be detected using the light distributed from the optical distributor, and a common sample arm commonly connected to the first and second interference parts;
   an optical switch connected to the first and second interference parts to select at least one of the interference signals transmitted from the first and second interference parts; and
   a detection unit for converting the interference signal selected by the optical switch according to a preset mode into an electrical signal,
   wherein the first interference part comprises: a first optical distributor for receiving the broadband light distributed from the main optical distributor; a first sample arm comprising a first sample arm collimator for receiving the light distributed from the first optical distributor; and a first reference arm comprising a first reference arm collimator for receiving the light distributed from the first optical distributor other than the light distributed to the first sample arm, and a first reference mirror for reflecting the light incident from the first reference arm collimator to allow the reflected light to return to the first optical distributor,
   wherein the second interference part comprises: a second optical distributor for receiving the broadband light distributed from the main optical distributor; a second sample arm comprising a second sample arm collimator for receiving the light distributed from the second optical distributor; and a second reference arm comprising a second reference arm collimator for receiving the light distributed from the second optical distributor other than the light distributed to the second sample arm, and a second reference mirror for reflecting the light incident from the second reference arm collimator to allow the reflected light to return to the second optical distributor, and wherein the common sample arm comprises:
a common arm optical distributor for reflecting the light transmitted from the first optical distributor and the second optical distributor through the first sample arm collimator and the second sample arm collimator;
a common arm optical scanner for irradiating the light reflected from the common arm optical distributor toward the different focused areas of the object to be detected; and
a common arm objective lens for focusing the light irradiated from the common arm optical scanner to allow the focused light to be irradiated onto the different focused areas of the object to be detected, and re-transmitting the light reflected from the different focused areas of the object to be detected to the common arm optical scanner.

2. The dual focusing optical coherence imaging system according to claim 1, wherein the common sample arm further comprises a first sample arm focusing lens between the first sample arm collimator and the common arm optical distributor.

3. A dual focusing optical coherence imaging system comprising:
a light source unit for generating broadband light;
a main optical distributor for distributing the light generated from the light source to allow the light to be propagated;
an interference unit including first and second interference parts for forming interference signals with respect to different focused areas of an object to be detected using the light distributed from the optical distributor, and a common sample arm commonly connected to the first and second interference parts for forming an optical path difference of the light irradiated onto different focused areas of the to-be-detected object from the first and second interference parts between the different focused areas;
an optical switch connected to the first and second interference parts to select at least one of the interference signals transmitted from the first and second interference parts; and
a detection unit for converting the interference signal selected by the optical switch according to a preset mode into an electrical signal,
wherein the first interference part comprises: a first optical distributor for receiving the broadband light distributed from the main optical distributor; a first sample arm comprising a first sample arm collimator for receiving the light distributed from the first optical distributor; and a first reference arm comprising a first reference arm collimator for receiving the light distributed from the first optical distributor other than the light distributed to the first sample arm, and a first reference mirror for reflecting the light incident from the first reference arm collimator to allow the reflected light to return to the first optical distributor,
wherein the second interference part comprises: a second optical distributor for receiving the broadband light distributed from the main optical distributor; a second sample arm comprising a second sample arm collimator for receiving the light distributed from the second optical distributor; and a second reference arm comprising a second reference arm collimator for receiving the light distributed from the second optical distributor other than the light distributed to the second sample arm, and a second reference mirror for reflecting the light incident from the second reference arm collimator to allow the reflected light to return to the second optical distributor, and wherein the common sample arm comprises:
a common arm optical distributor for reflecting the light transmitted from the first optical distributor and the second optical distributor through the first sample arm collimator and the second sample arm collimator;
a common arm optical scanner for irradiating the light reflected from the common arm optical distributor toward the different focused areas of the object to be detected; and
a common arm optical path dispersion unit for irradiating the light irradiated from the common arm optical scanner onto the different focused areas of the to-be-detected object, and re-transmitting the light reflected from the different focused areas of the to-be-detected object to the common arm optical scanner, the common arm optical path dispersion unit being disposed between the to-be-detected object and the common arm optical scanner to form an optical path difference of the light irradiated onto different focused areas of the to-be-detected object from the first and second interference parts between the different focused areas.

4. The dual focusing optical coherence imaging system according to claim 3, wherein the common arm optical path dispersion unit comprises:
a first dispersion optical distributor for distributing the light irradiated from the optical scanner so as to allow a first sample optical path to be formed in the same direction as the propagating direction of the light irradiated from the optical scanner and allow a second sample optical path to be formed in a direction perpendicular to the propagating direction of the light irradiated from the optical scanner;
a second dispersion optical distributor disposed between the first dispersion optical distributor and the to-be-detected object so as to confront the first dispersion optical distributor in such a manner as to be positioned on the first sample optical path and the second optical path;
a dispersion objective lens disposed between the second dispersion optical distributor and the to-be-detected object so as to allow the light transmitted through the second dispersion optical distributor to be focused on different focused areas of the to-be-detected object and allow the light reflected from the to-be-detected object to be transmitted to the second dispersion optical distributor;
a second dispersion sample optical path mirror disposed on the second sample optical path so as to allow the second sample optical path to be formed different from the first sample optical path; and
a second dispersion sample optical path focusing lens disposed on a partial path of the second sample optical path, which does not intersect the first sample optical path.

5. The dual focusing optical coherence imaging system according to claim 4, wherein the second dispersion sample optical path focusing lens is disposed between the first dispersion optical distributor and the second dispersion sample optical path mirror.

6. The dual focusing optical coherence imaging system according to claim 3, wherein the common arm optical path dispersion unit comprises:
- a first dispersion optical distributor for distributing the light irradiated from the optical scanner so as to allow a first sample optical path to be formed in the same direction as the propagating direction of the light irradiated from the optical scanner and allow a second sample optical path to be formed in a direction perpendicular to the propagating direction of the light irradiated from the optical scanner;
- a second dispersion optical distributor disposed between the first dispersion optical distributor and the to-be-detected object so as to confront the first dispersion optical distributor in such a manner as to be positioned on the first sample optical path and the second optical path;
- a second dispersion sample optical path mirror disposed on the second sample optical path so as to allow the second sample optical path to be formed different from the first sample optical path; and
- a first dispersion sample optical path focusing lens disposed on a partial path of the first sample optical path, which does not intersect the second sample optical path so as to allow the light transmitted through the second dispersion optical distributor to be focusingly irradiated onto a first focused area of the to-be-detected object; and
- a second dispersion sample optical path focusing lens disposed on a partial path of the second sample optical path, which does not intersect the first sample optical path so as to allow the light transmitted through the second dispersion optical distributor to be focusingly irradiated onto a second focal area different from the first focused area of the to-be-detected object.

7. The dual focusing optical coherence imaging system according to claim 3, wherein the first reference arm comprises a first reference optical path formed between the first reference arm collimator and the first reference mirror,
the second reference arm comprises: a second reference optical path formed between the second reference arm collimator and the second reference mirror, and
the interference unit comprises at least one common reference optical distributor through which the light on the first reference optical path and the light on the second reference optical path are passed commonly.

8. The dual focusing optical coherence imaging system according to claim 7, wherein the first reference arm comprises:
- a first dispersion reference optical path optical distributor for transmitting light incident through the common reference optical distributors;
- a first dispersion reference optical path mirror for reflecting the light exiting the first dispersion reference optical path optical distributor; and
- a first dispersion reference optical path lens for allowing the light reflected from the first dispersion reference optical path mirror to be focused on the surface of the first reference mirror.

9. The dual focusing optical coherence imaging system according to claim 7, wherein the second reference arm comprises:
- a second dispersion reference optical path optical distributor for transmitting light incident through the common reference optical distributors;
- a second dispersion reference optical path mirror for reflecting the light exiting the second dispersion reference optical path optical distributor; and
- a second dispersion reference optical path lens for allowing the light reflected from the second dispersion reference optical path mirror to be focused on the surface of the second reference mirror.

10. The dual focusing optical coherence imaging system according to claim 3, wherein the first interference part comprises a first reference polarization controller provided between the first optical distributor and the first reference arm collimator, and the second interference part comprises a second reference polarization controller provided between the second optical distributor and the second reference arm collimator.

11. The dual focusing optical coherence imaging system according to claim 3, wherein the optical switch is connected to the first optical distributor and the second optical distributor to receive the interference signals from the first optical distributor and the second optical distributor for transmission to the detection unit, and the dual focusing optical coherence imaging system further comprises a switching polarization controller disposed at an at least one position of positions between the optical switch and the first optical distributor/the second optical distributor and between the optical switch and the detection unit.

12. The dual focusing optical coherence imaging system according to claim 3, wherein the to-be-detected object is an eyeball, and one of the different focused areas to which the light is transmitted from the first sample arm collimator is a cornea.

13. The dual focusing optical coherence imaging system according to claim 12, wherein the other of the different focused areas to which the light is transmitted from the first sample arm collimator is a retina.

14. The dual focusing optical coherence imaging system according to claim 3, wherein the detection unit comprises:
- a detection collimator for allowing the interference signal selected by the optical switch to exit as parallel light;
- a detection grating for allowing the parallel light incident from the detection collimator to be diffracted;
- a detection lens for allowing the light diffracted by the detection grating to be focusingly transmitted; and
- a detector for converting the diffracted light incident from the detection lens into an electrical signal.

15. The dual focusing optical coherence imaging system according to claim 3, further comprising an optical isolator or an optical circulator disposed between the light source unit and the main optical distributor for allowing the light generated from the light source unit to be transmitted to only the main optical distributor.

16. The dual focusing optical coherence imaging system according to claim 3, wherein at least one of the optical distributors included in the main optical distributor and the interference unit comprises an optical fiber distributor.

17. The dual focusing optical coherence imaging system according to claim 3, further comprising:
- a control unit for receiving the electrical signal from the detection unit;
- a storage unit connected to the control unit for storing preset data therein;
- a calculation unit for executing a calculation operation and calculating video information in response to a control signal generated from the control unit based on the electrical signal applied to the control unit from the detection unit and the preset data stored in the storage unit; and a display unit for displaying an image of the video information thereon in response to an image control signal from the control unit.

18. The dual focusing optical coherence imaging system according to claim 3, wherein the light source unit comprises a wavelength-tunable light source.

19. The dual focusing optical coherence imaging system according to claim 3, wherein the detection unit comprises a photodiode or photodetector for converting the interference signal selected by the optical switch into the electrical signal.

20. The dual focusing optical coherence imaging system according to claim 3, wherein a part of the first interference part and the second interference part, and the common sample arm constitute a hand-held probe.

* * * * *